(12) United States Patent
Kalgutkar et al.

(10) Patent No.: US 6,762,182 B1
(45) Date of Patent: *Jul. 13, 2004

(54) CONVERTING COX INHIBITION COMPOUNDS THAT ARE NOT COX-2 SELECTIVE INHIBITORS TO DERIVATIVES THAT ARE COX-2 SELECTIVE INHIBITORS

(75) Inventors: Amit S. Kalgutkar, Nashville, TN (US); Lawrence J. Marnett, Nashville, TN (US)

(73) Assignee: Vanderbilt University, Nashville, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/869,384

(22) PCT Filed: Dec. 16, 1999

(86) PCT No.: PCT/US99/30219

§ 371 (c)(1),
(2), (4) Date: Aug. 21, 2001

(87) PCT Pub. No.: WO00/40087

PCT Pub. Date: Jul. 13, 2000

Related U.S. Application Data

(60) Provisional application No. 60/115,090, filed on Jan. 7, 1999.

(51) Int. Cl.[7] .......................................... A61K 31/501
(52) U.S. Cl. .......................... 514/235.2; 514/252.06; 514/339; 514/363; 514/365; 514/374; 514/378; 514/406; 514/415; 514/419; 514/420; 514/422
(58) Field of Search .......................... 514/235.2, 339, 514/252.06, 419, 363, 365, 374, 378, 406, 415, 422, 420

(56) References Cited

U.S. PATENT DOCUMENTS

| | | | |
|---|---|---|---|
| 3,161,654 A | 12/1964 | Shen | 260/319 |
| 3,285,908 A | 11/1966 | Shen | 260/211 |
| 3,336,194 A | 8/1967 | Shen | 167/65 |
| 3,654,349 A | 4/1972 | Shen | 260/515 M |
| 3,725,548 A * | 4/1973 | Shen et al. | 514/517 |
| 4,229,447 A | 10/1980 | Porter | 424/244 |
| 4,412,994 A | 11/1983 | Sloan et al. | 424/248 |
| 4,851,426 A | 7/1989 | Ladkani et al. | 514/420 |
| 5,016,652 A | 5/1991 | Rose et al. | 131/270 |
| 5,032,588 A | 7/1991 | Brooks et al. | 514/224.8 |
| 5,436,265 A | 7/1995 | Black et al. | 514/420 |
| 5,504,086 A | 4/1996 | Ellinwood, Jr. et al. | 514/252 |
| 5,510,368 A | 4/1996 | Lau et al. | 514/419 |
| 5,607,966 A | 3/1997 | Hellberg et al. | 514/458 |
| 5,681,964 A | 10/1997 | Ashton et al. | 548/491 |
| 5,811,438 A | 9/1998 | Hellberg et al. | 514/458 |
| 6,048,850 A | 4/2000 | Young et al. | 514/491 |
| 6,306,890 B1 * | 10/2001 | Kalgutkar et al. | 514/419 |

FOREIGN PATENT DOCUMENTS

| | | |
|---|---|---|
| CS | 190749 | 12/1981 |
| DE | 2735537 | 2/1979 |
| DE | 2926472 | 1/1981 |
| DE | 3145465 | 5/1983 |
| DE | 3235850 | 8/1983 |
| DE | 3206885 | 9/1983 |
| EP | 51278 | 5/1982 |
| EP | 144845 | 6/1985 |
| EP | 327766 | 8/1989 |
| EP | 335164 | 10/1989 |
| EP | 342682 | 11/1989 |
| ES | 432545 | 11/1976 |
| FR | 2392008 | 12/1978 |
| JP | 54090174 | 7/1979 |
| JP | 58201763 | 11/1983 |
| JP | 5916358 | 9/1984 |
| JP | 61060649 | 3/1986 |
| JP | 63196598 | 8/1988 |
| JP | 63275593 | 11/1988 |
| NL | 8105139 | 6/1982 |
| WO | WO95/04030 | 2/1995 |
| WO | WO95/20567 | 8/1995 |

OTHER PUBLICATIONS

Phelan et al., *Improved Delivery Through Biological Membranes, XXXVII, Synthesis and Stability of Novel Redox Derivatives of Naproxen and Indomethacin*, Pharmaceutical Research 6(8):667–676 (1989).

Otis et al., *Synthesis and Pharmaacological Evaluation of Amide Derivatives of Non–Steroidal Anti–Inflammatory Drugs*, Inflammopharmacology 1:201–212 (1992).

Allison et al., *Gastrointestinal Damage Associated with the Use of Nonsteroidal Antiinflammatory Drugs*, The New England Journal of Medicine 327(11):749–754 (Sep. 10, 1992).

Black et al., *From Indomethacin to Selective COX–2 Inhibitor: Development of Indolalkanoic Acids as Potent and Selective Cyclooxygenase–2 Inhibitors*, Bioorganic & Medicinal Chemsitry Letters 6(6):725–720 (1996).

Devane et al., *Isolation and Structure of a Brain Constituent That Binds to the Cannabinoid Receptor*, Science 258:1946–1949 (Dec. 18, 1992).

Chan et al., *Pharmacology of a Selective Cyclooxygenase–2 Inhibitor, L–745,337: A Novel Nonsteroidal Anti–Inflammatory Agent with an Ulcerogenic Sparing Effect in Rat and Nonhuman Primate Stomach*, J. of Pharmacology and Experimental Therapeutics 274(3):1531–1537 (1995).

DeWitt et al., *Primary structure of prostaglandin G/H synthase from sheep vesicular gland determined from the complementaty DNA sequence*, Proc. Natl. Acad. Sci. USA 85:1412–1416 (Mar. 1988).

(List continued on next page.)

Primary Examiner—Dwayne C. Jones
(74) Attorney, Agent, or Firm—Jenkins, Wilson & Taylor, P.A.

(57) ABSTRACT

A method of altering specificity of cyclooxygenase-inhibiting compounds that have a COOH moiety by changing the various COOH containing compounds, such as indomethacin, into ester derivatives or into secondary amide derivatives.

16 Claims, No Drawings

OTHER PUBLICATIONS

Downing et al., *Enzyme Inhibition by Acetylenic Compounds*, Biochemical and Biophysical Research Communications 40(1):218–223 (1970).

Downing et al., *Structural Requirements of Acetylenic Fatty Acids for Inhibition of Soybean Lipoxygenase and Prostaglandin Synthetase*, Biochimica et Biphysica ACTA 280:343–347 (1972).

Diago–Meseguer et al., *A New Reagent for Activating Carboxyl Groups; Preparation and Reactions of N,N–Bis [2–oxo–3–ox–azolidinyl]phosphorodiamidic Chloride*, Communicaitons pp547–551 (Jul. 1980).

Futaki et al., *NS–398, a new anti–inflammatory agent, selectively inhibits prostaglandin G/H synthase/cyclooxygenase (COX–2) activity in vitro*, Prostaglandins 47:55–59 (Jan. 1994).

Gans et al., *Anti–inflammatory and Satety Profile of DuP 697, a Novel Orally Effective Prostaglandin Synthesis Inhibitor*, J. of Pharmacology and Experimental Therapeutics 254(1):180–187 (1990).

Graedon et al., *Pills promise relief without ulcers*, The News & Observer (People's Pharmacy) p. 8D (Sep. 13, 1998) (Newspaper article).

Hla et al. et al., *Human cyclooxygenase–2 cDNA*, Proc. Natl. Acad. Sci. USA 89:7384–7388 (1992).

Kalgutkar et al., *Aspirin–like Molecules that Covalently Inactivate Cyclooxygenase–2*, Science 280:1268–1270 (May 22, 1998).

Katori et al., *Induction of Prostaglandin H Synthase–2 in Rat Carrageenin–Induced Pleurisy and Effect of a Selectrive COX–2 Inhibitor*, Advances in Prostaglandin, Thromboxane, and Leukotriene Research 23:345–347 (1995).

Kennedy et al., *Cloning and Expression of Rat Prostaglandin Endoperoxide Synthase (Cyclooxygenase)–2 cDNA[1]*, Biochemical and Biohysical Research Communications 197(2):494–500 (Dec. 15, 1993).

Khanna et al., *1,2–Diarylpyrroles as Potent and Selective Inhibitors of Cyclooxygenase–2*, Journal of Medicinal Chemistry 40(11):1619–1633 (1997).

Khanna et al., *1,2–Diarylimidazoles as Potent Cyclooxygenase–2 Selective, and Orally Active Antiinflammatory Agents*, Journal of Medicinal Chemistry 40(11):1634–1647 (1997).

Kolasa et al., *Nonsteroidal Anti–Inflammatory Drugs as Scaffolds for the Design of 5–Lipoxygenase Inhibitos*, Journal of Medicinal Chemsitry 40:519–824 (1997).

Kujubu et al., *TIS10, a Phorbol Ester Tumor Promoter–inducible mRNA from Swiss 3T3 Cells, Encodes a Novel Prostaglandin Synthase/Cyclooxygenase Homologue*, The Journal of Biological Chemistry 266(20):12866–12872 (1991).

Lee et al., *Selective Expression of Mitogen–inducible Cyclooxygenase in Macrophages Stimulated with Lipopolysaccharide*, The Journal of Biological Chemistry 267:25934–25938 (1992).

Li et al., *Cyclooxygenase–2 Inhibitors. Synthesis and Pharmacological Activites of 5–Methanesulfonamido–1–indanone Derivatives*, The Journal of Medicinal Chemistry 38:4897–4905 (1995).

Li et al., *1,2–Diarylcyclopentenes as Selective Cycloozygenase–2 Inhibitors and Orally Active Anti–inflammatory Agents*, Journal of Medicinal Chemistry 38:4570–4578 (1995).

Li et al., *Novel Terphenyls as Selective Cyclooxygenase–2 Inhibitors and Orally Active Anti–inflammatory Agents*, Journal of Medicinal Chemsitry 39:1846–1856 (1996).

Linari et al., *Substituted Anilides of 1–(p–Chlorobenzoyl)–5–methoxy–2–methyl–indole–3–acetic Acid*, Istituto Farmaco Biologico Stroder, Firenze, Italy pp:89–91 (1973).

Luong et al., *The Structure of Human Cyclooxygenase–2: Conservation and Flexibility of the NSAID Binding Site*, Nature Structural Biology 3:927–933 (1996).

Masferrer et al., *Selective inhibition of inducible cyclooxygenase 2 in vivo is anti–inflammatory and nonulcerogenic*, Proc. Natl. Acad. Sci. USA 91:3228–3232 (Apr. 1994).

Meade, et al., *Differential Inhibition of Prostaglandin Endoperoxide Synthase (Cyclooxygenase) Isozymes by Aspirin and Other Non–Steroidal Anti–inflammatory Drugs*, The Journal of Biological Chemistry 235(9):6610–6614 (1993).

Nakamura et al., *Studies on Antiinflammatory Agents. II.[1) Synthesis and Pharmacological Properties of 2'–(Phenylthio) methanesulfonanilides and Related Derivatives*, Chem. Pharm. Bull. 41(5):894–906 (1993).

Ogiso et al., *Pharmacokinetics of indomethacin ester prodrugs: gastrointestinal and hepatoc toxicity and the hydrolytic capacity of various tissues in rats*, Biol. Pharm. Bull. 19(9):1178–1183 (Sep. 1996) (Abstract).

O'Sullivan et al, *Lipopolysaccharide–induced expression of prostaglandin H synthase–2 in alveolar macrophages is inhibited by dexamethasone but not by aspirin*, Biochemical and Biophysical Research Communications 191(3):1294–1300 (Mar. 31, 1993).

Physicians' Desk Reference, edition 41 pp:1305–1310 (1987).

Prasit et al., *L–745,337: A Selective Cyclooxygenase–2 Inhibitor*, Med. Chem. Res. 5:364–374 (1995).

Ramesha, *Human and Rat Cyclooxygenases are Pharmnacologically Distinct, Eicosanoids and other Bioactive Lipids in Cancer Inflammation and Radiation Injury* 3:67–71 (1997).

Reitz et al., *Novel 1,2–Diarylcyclopentenes are Selective, Potent, and Orally Active Cyclooxygenase Inhibitos*, Medicinal Chemistry Research 5:351–363 (1995).

Riendeau et al., *Biochemical and Pharmacological Profile of a Tetrasubstituted Furanone as a Highly Selective COX–2 Inhibitor*, British Journal of Pharmacology, 121:105–117 (1997).

Roy et al., *A New Series of Selective COX–2 Inhibitors: 5,6–Diarylthiazolo[3,3–b][1,2,4]Triazoles*, Bioorganic & Medicinal Chemistry Letters, 7(1):57–62 (1997).

Sauvaire et al., *Pharmacological Activity and Toxicity of Apyramide: Comparison with Non–Steroidal Anti–Inflammatory Agents*, Drugs Exp Clin Res 13(5):247–252 (1987).

Smith et al., *Prostaglandin Endoperoxide H Synthases (Cyclooxygenases)–1and –2*, The Journal of Biolgical Chemsitry, 271(52): 33157–33160 (Dec. 26, 1996).

Tanaka et al., *Pharmacological Studies of the New Antiinflammatory Agent 3–Formylamino–7–methylsulfonylamino–6–phenoxy–4H–1–benzopyran–4–one*, Arzneim.–Forsch./Drug Res., 42(7):935–944 (1992).

Therien et al, *Synthesis and Biological Evaluation of 5,6–Diarylimidazo[2. 1–b]Thiazole as Selective COX–2 Inhibitors*, Bioorganic & Medical Chemistry Letters, 7(1):47–52 (1997).

Tsuji et al., *Studies on Anti–inflammatory Agents. IV. Synthesis and Pharmacological Properties of 1,5–Diarylpyrazoles and Related Derivatives, Chem. Pharm. Bull.*, 45(6):987–995 (1997).

Vane et al., *Inducible Isoforms of Cyclooxygenase and Nitric–oxide Synthase in Inflammation, Proc. Natl. Acad. Sci. USA*, 94:2046–2050 (Mar. 1994).

Pal et al., *7–Oxabicycloheptylprostanoic Acids: Potent, Time–Dependent Cyclooxy–genase Inhibitors that Induce a Conformational Change in the Prostaglandin Endoperoxide Synthase Protein, Journal of Medicinal Chemistry*, 35:2340–2342 (1992).

Flynn et al., *Nonsteroidal Antiinflammatory Drug Hydroxamic Acids, Dual Inhibitors of Both Cyclooxygenase and 5–Lipoxygenase, Journal of Medicinal Chemistry*, 33:2070–2072 (1990).

Wiesenberg–Boettcher et al., *The Pharmacological Profile of CGP 28238, a Novel Highly Potent Anti–Inflammatory Compound, Drugs Exp Clin Res*, 15(11–12):501–509 (1989).

Yu et al., *Synthesis of Prostaglandin $E_2$ Ethanolamide from Anandamide by Cyclooxygenase–2, The Journal of Biological Chemistry*, 272(34):21181–21186 (Aug. 22, 1997).

Yokoyama et al., *Cloning of Human Gene Encoding Prostaglandin Endoperoxide Synthase and Primary Structure of the Enzyme, Biochemcial and Biophysical Research Communications*, 165(2):888–894 (Dec. 15, 1989).

McMurry, *Carboxylic Acid Derivatives, Organic Chemistry*, 742–745 (1988).

Boltze et al., *Chemical Structure and Antiinflammatory Activity in the Group of Substituted Indole–3–Acetic Acids, Arzneim.–Forsch.*, 30(8A):1314–1325 (1980).

Tammara et al., *Synthesis and Evaluation of Morpholinoalkyl Ester Prodrugs of Indomethacin and Naproxen, Pharm. Res.*, 10(8):1191–1199 (1993).

Fisnerova et al., "Pharmacologically Interesting Indomethacin Derivates," Heterocycles, p. 373, (1978).

Diago–Meseguer et al., "A New Reagent for Activating Carboxyl Groups; Preparation and Reactions of N,N–Bis [2–oxo–3oxazolidinyl]phosphoradiamidic Chloride," Synthesis, p. 547–551, (Jul. 30, 1980).

Linari et al., "Substituted Anilides of 1–(p–Chlorobenzoyl)–5–methoxy–2–methylindole–3–3acetic Acid," Arzneim–Foprsch. (Drug Research), vol. 23 (No. 1), p. 89–91, (1973).

Tammara et al., "Synthesis and Evaluation of Morpholinoalkyl Ester Prodrugs of Indomethacin and Naproxen," Pharmaceutical Research, vol. 10 (No. 8), p. 1191–1199, (1993).

Katori et al., "Induction of Prostaglandin H Synthase–2 in Rat Carrgeenin–induced Pleurisy and Effect of a Selective Cox–2 Inhibitor," Advances in Prostaglandin, Thromboxane, and Leukotriene Reserach, p. 345–347, (1995).

Dewitt et al., "Primary Structure of Prostaglandin G/H Synthase from Sheep Vesicular Gland Determined from the COmplementary DNA Sequence," Proc. Natl. Acad. Sci. USA, p. 1412–1416, (1988).

Smith et al., "Prostaglandin Endoperoxide H Synthases (Cyclooxygenases)–1 and 2," The Journal of Biological Chemistry, vol. 271 (No. 52), p. 33157–33160, (Dec. 27, 1996).

Yokoyama et al., "Cloning of Human Gene Encoding Prostaglandin Endoperoxide Synthase and Primary Structure and Enzyme," Biochemical and Biophysical Research Communications, vol. 165 (No. 2), p. 888–894, (Dec. 15, 1989).

HLA et al., "Human Cyclooxygenase–2 cDNA," Proc Natl. Acad. USA, p. 7384–7388, (Aug. 30, 1992).

Kujubu et al., "TIS10, a Phorbol Ester Tumor Promoter–inducible mRNA from Swiss 3T3 Cells, Encodes a Novel Prostaglandin Synthase/Cyclooxgenase Homologue," The Journal of Biological Chemsitry, vol. 266 (No. 20), p. 12866–12872, (Jul. 15, 1991).

Allison et al., "Gastrointestinal Damage Asociated with the Use of Nonsteroidal Antiinflammatory Drugs," the New England Journal of Medicine, vol. 327 (No. 11), pp. 749–754, (Sep. 10, 1992).

Lee et al., "Selective Expression of Mitogen–inducible Cyclooxygenase in Macrohages Stimulated with Lipopolysaccharide," The Journal of Biological Chemistry, p. 25934–25938, (Dec. 25, 1992).

Penning et al., "Synthesis and Biological Evaluation of the 1,5–Dairylpyrazole Class of Cyclooxygenase–2 Inhibitors: Indentification of 4–[5(4–Methylphenyl)–3–(trifluoromethyl)–1H–pyrazol–lyl]benzenesulfonamide (SC–58635, Celecoxib," J. Med Chem., p. 1347–1365, (1997).

Gans et al., "Anti–Inflammatory and Safety Profile of DuP 697, a Novel Orally Effective Prostaglandin Synthesis Inhibitor," The Journal of Pharmacology and Experimental Therapeutics, vol. 254 (No. 1), p. 180–187, (1990).

Khanna et al., "1,2–Diarylimidazoles as Potent, Cyclooxygenase–2 Selective, and Orally Active Antiinflammatory Agents," Journal of Medicinal Chemistry, vol. 40 (No. 1), p. 180–187, (1997).

Vane et al., "Inducible Isoforms of Cyclooxygenase and Nitric–Oxide Synthase in Inflammation," Proc. Natl. Acad. Sci. USA, p. 2046–2050, (Mar. 30, 1994).

Masferrer et al., "Selective Inhibition of Inducible Cyclooxygenase 2 In Vivo is Antiinflammatory and Nonuclerogenic," Proc. Natl. Acad. Sci. USA, p. 3228–3232, (1994).

O'Sullivan et al., "Lipopolyusaccharide–induced Expression of Prostaglandin H Synthase–2 in Alveolar Macrophages in Inhibitied by Dexamethasone but not by Aspirin," Biochemical and Biophysical Research Communications, vol. 191 (No. 3), p. 1294–1300, (Mar. 31, 1993).

Kennedy et al., "cloning and Expression of Rat Prostaglandin Endoperoxide Synthase (Cyclooxygenase)–2 cDNA," Biochemical and Biophysical Research Communications, vol. 197 No. 2), p. 494–500, (Dec. 15, 1993).

Khanna et al., "1,2–Diarylpyrroles as Potent and Selective Inhibitors of Cyclooxygenase–2," Journal of Medicinal Chemistry, vol. 40 (No. 11), p. 1619–1633, (1997).

Meade et al., "Differential Inhibition of prostaglandin Endoperoxide Synthase (Cyclooxygenase) Isozymes by Aspirin and Other Non–steroidal Anti–inflammatory Drugs," vol. 238 (No. 9), p. 610–6614, (Mar. 25, 1993).

Futaki et al., "NS–398, a New Ati–inflammatory Agent, Selectively Inhibits Prostaglandin G/H Synthase–cyclooxygenase (COS–2) Activity In Vitro," Pharmaceutical Research, p. 55–59, (Jan. 30, 1994).

Li et al., "Novel Terphenyls as 'selective Cyclooxygenase–2 Inhibitors and Orally Active Anti–Inflammatory Agents," J. Med. Chem., p. 1846–1856, (1996).

Riendeau et al, "Biochemical and Pharmacological Profile of a Tetrasubstituted Furanone as a Highly Selective COX–2 Inhibitor," British Journal of Pharmacology, p. 105–117, (1997).

Tsuji et al., "Studies on Anti–inflammatory Agents. IV. Synthesis and Pharmacological Properties of 1,5–Diarylpyrazoles and Related Derivatives," Chem., Pharm. bull., p. 987–995, (Jun. 30, 1997).

Therien et al., "Synthesis and biiological Evaluation of 5,6–Diarylimidazo[2.1–b]Thiazole as Selective COX–2 Inhibitors," Bioorganic & Medicinal Chemistry Letters, vol. 7 (No. 1), p. 47–52, (1997).

Roy et al., "A New Serie sof Selective COX–2 Inhibitors; 5,6–Diarylthiazolo[3,2–b][1,2,4]Triazoles," Bioorganic & Medicinal Chemistry Letters, vol. 7 (No. 1), p. 57–62, (1997).

Li et al.,"1,2–Diarylcyclopentenes as Selective Cyclooxygenas–2 Inhibitors and Orally Active Anti–Inflammatory Agents," J. Med. Chem., p. 4570–4578, (1996).

Reitz et al., "Novel 1,2–Diarylcyclopentenes ar eSelective, Potent, and Orally Active Cyclooxygenase Inhibitos," Med. Chem. Res., p. 351–363, (1995).

Li et al., "Cyclooxygenase–2 Inhibitors. Synthesis and Pharmacological Activites of 5–Methanesulfonamido–1–indanone Derivatives," Journal of Medicinal Chemistry, p. 4897–4905 (1995).

Downing et al., "Structural 'requirements of Acetylenic Fatty Acids for Inhibition of Soybean Lipoxygenase and Prostaglandin Synthetase," Biochem. Biophys. Acta., p. 343–347, (1972).

Downing et al., "Enzyme Inhibition by Acetylenic Compounds," Biochemical and Biophysical Communications, vol. 40 (No. 1), p. 218–223, (1970).

Devane et al., "Isolation and Structure of a Brain Constituent that binds to the Cannabinoid Receptor," Science, p. 1946–1949, (Dec. 18, 1992).

Remesha, "Human and Rat Cyclooxygenases are Pharmacologically Distinct," Eicosanoids and Other Bioactive Lipids in Cancer Inflammation Injury 3, p. 67–71, (1997).

Luong et al., "the Structure of Human Cyclooxygenase–2: Conservation and Flexibility of the NSAID Binding Site," Nature Structural Biology, p. 927–933, (1996).

Yu et al., "Synthesis of Prostaglandin E2 Ethanolammide from Anadamide by Cyclooxygenase–2," Journal of Biological Chemistry, vol. 272 (No. 34), p. 21181–2118, (Aug. 22, 1997).

Prasit et al., "L–745,337: A Selective Cycloxygenase–2 inhibitor," Med. Chem. Res., p. 364–374, (1995).

Pal et al., "7–Oxabicycloheptylprostanoic Acids: Potent, Time–Dependent cyclooxygenase Inhibitors that Induce a Conformational Change in the Prostaglandin Endoperoxide synthase Protein," Journal of Medicinal Chemistry, vol. 35 (No. 12), p. 2340–2342, (1992).

Kalgutkar et al., "Aspirin–like Molecules that Covalently Inactivate Cyclooxygenase–2," Science, p. 1268–1270, (May 22, 1998).

Flynn et al., "Nonsteroidal Antiinflammatory Drug Hydroxamic Acids," J. Med. Chem., p. 819–824, (1990).

Kolasa et al., "Nonsteroidal Anti–Inflammatory Drugs as Scaffolds for the Design of 5–Lipoxygenase Inhibitos," J. Med. Chem., p. 819–824, (1997).

Black et al., "From Indomethacin to a Selective COX–2 Inhibitor: Development of Indolalkanoic Acids as Potent and Selective COX–2 Inhibitor: Development of Indolalkanoic Acids as Potent and Selective Cyclooxygenase–2 Inhibitors," Bioorganic & Medicinal Chemstiyr Letters, vol. 6 (No. 6), p. 725–730, (1996).

Chan et al., "Pharmacology of a Selective Cyclooxygenase–2 Inhibitor, L–745, 337: A Novel Nonsteroidal Anti–inflammatory Agent with an Ulcerogenic Sparing Effect in Rat and Nonhuman Primate Stomach," vol. 274 (No. 3), p. 1531–1537, (1995).

Nakamura et al., "Studies on Antiinflammatory Agents II. Synthesis and Pharmacological Properties of 2'–(Phenylthio)methanesulfonanilides and Related Derivatives," Chem. Pharm. Bull., vol. 41 (No. 5), p. 894–906, (1993).

Boltze et al., "Chemical Structure and Anti0inflammatory Activity in the Group of Substituted Indole–3–acetic Acids," Arzneim–Forsch/Drug Res., vol. 30 (II), (No. 8a), p. 1314–1325, (1980).

Graedon et al., "Pills Promise Relief Without Ulcers," The News and Observer, p. 8D, (Sep. 13, 1998).

Ogiso et al., "Pharmacokinetics of Indomethacin Ester Prodrugs: Gastrointestinal and Hepatic Toxicity and Hydrolytic Capacity of Various Tissues in Rats," Biol. Pharm. Bull., vol. 19 (No. 9), p. 1178–1183, (Sep. 1, 1996).

Sauvaire et al., "Pharmacological Activity and toxicity of Apyramide: Comparison with Non–steroidal Anti–inflammatory Agents," Drugs Exp. Clin. Res., vol. 13 (No. 5), p. 247–252, (1987).

Weisenberg–Boettcher et al., "The Pharmacological Profile of CGP 28238, a Novel Highly Potent Anti–inflammatory Compound," Drugs Exp. Clin. res., vol. 13 (No. 5), p. 501–509, (1989).

Davaran et al., "Acrylic Type Polymers Containing Ibuprofen and Indomethacin with Disfunctional Spacer Group; Synthesis and Hydrolysis," J. Controlled Release, vol. 47 (No. 1) p. 41–49, (1997).

Kappe et al., "Non–steroidal Antiinflammatory Agents, V. Basic Esters of Indomethacin," J. Prakt Chem., vol. 332 (No. 4), p. 475–478, (1990).

Kwapiszewski et al., "Synthesis of N–[1–p–chlorobenzoyl)–5–methoxy–2–methyl–3–indole acetyl] Amino and their Esters," Acto. Pol. Pharm., vol. 39 (No. 5–6), p. 327–336, (1982).

Otis et al., "Synthesis and Pharmaological Evaluation of Amide Derivatives of Nonsteroidal Anti–inflammatory Drugs," Inflammopharmacology, vol. 1 (No. 3), p. 201–212, (1992).

Rojo et al., "Variable Effects of Indomethacin and Four Related Compounds on Lymphocyte Blastogenesis and Cell–mediated Cytotoxicity," Int. J. Clin. Pharmocol., Ther. Toxicol., vol. 19 (No. 9), p. 420–424, (1981).

Svoboda et al., "Potential Anti–inflammatory Agents Based on Indomethacin Esters," Cesk Farm., vol. 40 (No. 2), p. 71–4, (1991).

Phelan et al., "Improved Delivery Through Biological Membranes. XXXVII. Synthesis and Stability of Novel Redox Derivatives of Naproxen and Indomethacin," Pharm. Res., vol. 6 (No. 8), p. 667–676, (1989).

McClean et al., "Synthesis and Pharmacological Evaluation of Congugates of Prednisolone and Non–steroidal Anti–inflammatory Agents," Steroids, vol. 54 (No. 4), p. 421–439, (1989).

Makovec et al., "Pharmacokinetics and Metabolism of [14C]–progulmetacin after Oral Administration in the Rat," Arzneim.–Forsch., vol. 37 (No. 7), p. 806–813, (1987).

Boltze et al., "Chemnical Structure and Anti–inflammatory Activity in the Group of Substituted Indole–3–acetic Acids," Arzneim.–Forsch., vol. 30 (No. 8A), p. 1314–1325, (1980).

Rojo et al., "Variation in the Immunosuppressive Activity by Structural Modifications of a Serie of NOn–steroidal Anti-inflammatory Drugs (Indomethacin Esters)," Arch. Farmacol. Toxicol., vol. 4 (No. 3), p. 287–292, (1978).

Barasoain et al.,"Indomethacin Esters Acting as Anti–inflammatory and Immunosuppressive Drugs," Int. J. Clin. Pharmacol. Biopharm., vol. 16 (No. 5), p. 235–239, (1978).

Barasoain et al., "Immunosuppressive Effects of some Organic Compounds with Anti–inflammatory Activity," Chemother., Proc. Int. Cong. Chemother., p. 21–26, (1976).

Bonina et al., "In Vitro and In Vivo Evaluation of Polyoxyethylene Indomethacin Esters as Dermal Prodrugs," J. Controlled Release, vol. 34, No. 3 br273, p. 223–232, (1995).

Yamawaki et al., "Piperazinealkanol Ester Derivatives of Indomethacin as Dual Inhibitors of 5–lipoxygenase and Cyclooxgenase," Chem. Pharm. Bull., vol. 42 (No. 4), p. 963–971, (1994).

Decaprariis et al., "Synthesis and Pharmacological Evaluation of Oligoethylene Ester Derivatives as Indomethacin Oral Prodrugs," J. Pharm. Sci., vol. 83 (No. 11), p. 1578–1581, (1994).

Fishernova et al., "Esters of 1–(p–chlorobenzoyl)5–methoxy–2–methyl–3–indolylacetic Acid," Collect. Czech. Chem. Commun., vol. 45 (No. 3), p. 901–905, (1980).

Flynn et al., "Nonsteroidal Anti–inflammatory Drug Hydroxamic Acids. Dual Inhibitors of Both Cyclooxygenase and 5–lipoxygenase," J. Med. Chem., vol. 33 (No. 8), p. 2070–2072, (1990).

Physicians' Desk Reference, 41st Edition, pp. 1304–1310 (1987).

Fisnerova et al., "Esters of 1–(p–chlorobenzoyl)–5–methoxy–2methyl–3–indolylacetic acid," Heterocycles, p. 667, (May 1, 1981).

"Indole Acid Amides", vol. 62, Heterocyclic Compounds, pp 1697–16198, (1965).

"Pharmacologically Interesting Indomethacin Derivates", vol. 88, Heterocycles, p 373 (1978).

McMurray, "Organic Chemsitry," 2nd ed., p. 742–745 (1988).

* cited by examiner

CONVERTING COX INHIBITION COMPOUNDS THAT ARE NOT COX-2 SELECTIVE INHIBITORS TO DERIVATIVES THAT ARE COX-2 SELECTIVE INHIBITORS

CROSS REFERENCE TO RELATED APPLICATION

This application is based on and claims priority to PCT International Application No. PCT/US99/30219, filed Dec. 16, 1999 designating all states (including the United States) and published in English with an International Search Report on Jul. 13, 2000 as WO 00/40087, which itself claimed priority to U.S. Provisional Application Serial No. 60/115,090, filed Jan. 7, 1999, each of which are herein incorporated by reference in their entireties.

GOVERNMENT INTEREST

This research was funded by a research grant from the National Institutes of Health (Research Grant No. CA47479). Thus, the United States government has certain rights in the invention.

TECHNICAL FIELD

The present invention, in general, relates to ester derivatives and amide derivatives of various drugs, more specifically, such derivatives of non-steroidal antiinflammatory drugs (NSAIDs). Even more specifically, the present invention relates to ester derivatives and secondary amide derivatives of NSAIDs, particularly of indomethacin (an NSAID), that exhibit inhibition of cyclooxygenase-2(COX-2) far exceeding inhibition of cyclooxygenase-1(COX-1), and also, that still exhibit the analgesic, antiinflammatory, and/or antipyretic effect of the NSAID, in warm blooded vertebrate animals, including humans.

Table of Abbreviations

| Abbreviations | Definitions |
| --- | --- |
| NSAID | non-steroidal antiinflammatory drug |
| COOH | carboxylic acid moiety |
| COX | cyclooxygenase |
| $PGH_2$ | prostaglandin $H_2$ |
| $PGD_2$ | prostaglandin $D_2$ |
| PGHS | prostaglandin endoperoxide synthase |
| PER | peroxidase |
| SAR | structure-activity relationship |
| GI | gastrointestinal |
| $IC_{50}$ | concentration in $\mu M$ of indomethacin (or indomethacin derivative) at which there is 50% inhibition of COX activity--the lower $IC_{50}$ is, then the more potent the drug is |
| BOC | tert butoxy carbonyl |
| DMSO | dimethyl sulfoxide |
| $^{14}$C-AA | [1-$^{14}$C]-arachidonic acid |
| HPLC | high performance liquid chromatography |
| TLC | thin layer chromatography |
| mg | milligram |
| kg | kilogram |
| mL | milliliter |
| $\mu M$ | micromole/liter |
| $\mu L$ | microliter |
| N | normal (when used in conjunction with acid concentrations) |
| NMR | nuclear magnetic resonance |
| $Et_2O$ | diethyl ether |
| EtOAc | ethyl acetate |

-continued

Table of Abbreviations

| Abbreviations | Definitions |
| --- | --- |
| $Et_3N$ | triethyl amine |
| AcOH | acetic acid |
| $CDCl_3$ | deuteriated chloroform |
| rt | room temperature (about 72° F., 22° C.) |
| BOP-Cl | bis(2-oxo-3-oxazolidinyl)phosphonic chloride (sold by Aldrich in Wisconsin), and also see the journal article, Diago-Meseguer, Palomo-Coll, Fernandez-Lizarbe, and Zugaza-Bilbao, "New Reagent for Activating Carboxyl Groups; Preparation and Reactions of N,N-Bis[2-oxo-3-oxazolidinyl] phosphorodiamidic Chloride", Synthesis (1980) pp. 547–551 |
| mp | melting point |
| FBS | fetal bovine serum |
| DMEM | Dulbecco's modified essential medium |
| LPS | lipopolysaccharide |
| PBS | phosphate-buffered saline |
| IFN-g | interferon gamma |
| DCC | dicyclohexylcarboiimide |
| DMAP | 4-dimethylamino pyridine |

BACKGROUND OF THE INVENTION

As discussed in more detail below, the COX enzyme is really two enzymes, COX-1 and COX-2, which serve different physiological and pathophysiological functions. As is well known, at antiinflammatory and/or analgesic doses, indomethacin, aspirin, and other NSAIDs effect great inhibition of COX-1, which protects the lining of the stomach from acid, along with relatively minimal inhibition of COX-2, which provokes inflammation in response to joint injury or a disease like arthritis. Also, certain NSAIDs exhibit essentially the same inhibitory activity against both COX-1 and COX-2. Thus, zeroing in on inhibition of COX-2 alone has been the goal of drug developers for several years in order to reduce or eliminate the GI irritation caused by COX-1 inhibition.

More specifically, as discussed in Smith, Garavito, and DeWitt, "D. L. Prostaglandin Endoperoxide H Synthases (Cyclooxygenases)-1 and -2", J. Biol. Chem., (1996) Vol. 271, pp. 33157–33160, the pertinent step in prostaglandin and thromboxane biosynthesis involves the conversion of arachidonic acid to $PGH_2$, which is catalyzed by the sequential action of the COX and PER activities of PGHS, as set out in the following reaction scheme:

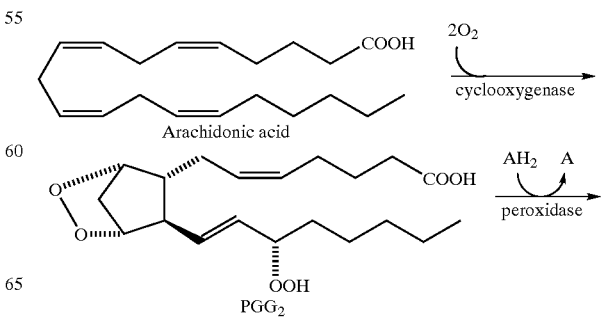

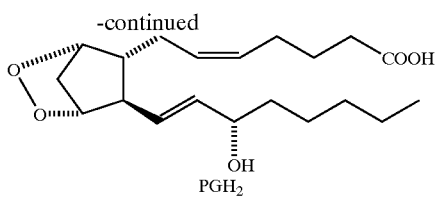

PGH$_2$

That COX activity originates from two distinct and independently regulated enzymes, termed COX-1 and COX-2, is described in DeWitt and Smith, "Primary Structure of Prostaglandin G/H Synthase from Sheep Vesicular Gland Determined from the Complementary DNA Sequence", *Proc. Natl. Acad. Sci. U.S.A.* (1988) Vol. 85, pp. 1412–1416; Yokoyama and Tanabe, "Cloning of Human Gene Encoding Prostaglandin Endoperoxide Synthase and Primary Structure of the Enzyme", *Biochem. Biophys. Res. Commun.* (1989) Vol. 165, pp. 888–894; and Hla and Neilson, "Human Cyclooxygenase-2-cDNA", *Proc. Natl. Acad. Sci. U.S.A.* (1992) Vol. 89, pp. 7384–7388.

COX-1 is the constitutive isoform and is mainly responsible for the synthesis of cytoprotective prostaglandins in the GI tract and for the synthesis of thromboxane, which triggers platelet aggregation in blood platelets. See, Allison, Howatson, Torrence, Lee, and Russell, "Gastrointestinal Damage Associated with the Use of Nonsteroidal Antiinflammatory Drugs", *N. Engl. J. Med.* (1992) Vol. 327, pp. 749–754.

On the other hand, COX-2 is inducible and short-lived. Its expression is stimulated in response toendotoxins, cytokines, and mitogens. See, Kujubu, Fletcher, Varnum, Lim, and Herschman, "TIS10, A Phorbol Ester Tumor Promoter Inducible mRNA from Swiss 3T3 Cells, Encodes a Novel Prostaglandin Synthase/Cyclooxygenase Homologue", *J. Biol. Chem.* (1991) Vol. 266, pp. 12866–12872; Lee, Soyoola, Chanmugam, Hart, Sun, Zhong, Liou, Simmons, and Hwang, "Selective Expression of Mitogen-Inducible Cyclooxygenase in Macrophages Stimulated with Lipopolysaccharide", *J. Biol. Chem.* (1992) Vol. 267, pp. 25934–25938; and O'Sullivan, Huggins, Jr., and Mccall, "Lipopolysaccharide-induced Expression of Prostaglandin H Synthase-2 in Aveolar Macrophages is Inhibited by Dexamethasone by not by Aspirin", *Biochem. Biophys. Res. Commun.* (1993) Vol. 191, pp. 1294–1300.

Importantly, COX-2 plays a major role in prostaglandin biosynthesis in inflammatory cells (monocytes/macrophages) and in the central nervous system. See, Masferrer, Zweifel, Manning, Hauser, Leahy, Smith, Isakson, and Seibert, "Selective Inhibition of Inducible Cyclooxygenase-2 in vivo is Antiinflammatory and Nonulcerogenic", *Proc. Natl. Acad. Sci. U.S.A.* (1994) Vol. 91, pp. 3228–3232; Vane, Mitchell, Appleton, Tomlinson, Bishop-Bailey, Croxtall, and Willoughby, "Inducible Isoforms of Cyclooxygenase and Nitric Oxide Synthase in Inflammation", *Proc. Natl. Acad. Sci. U.S.A.* (1994) Vol. 91, pp. 2046–2050; Harada, Hatanaka, Saito, Majima, Ogino, Kawamura, Ohno, Yang, Katori, and Yamamoto, "Detection of Inducible Prostaglandin H Synthase-2 in Cells in the Exudate of Rat Carrageenin-Induced Pleurisy", *Biomed. Res.* (1994) Vol. 15, pp. 127–130; Katori, Harada, Hatanaka, Kawamura, Ohno, Aizawai, and Yamamoto, "Induction of Prostaglandin H Synthase-2 in Rat Carrageenin-Induced Pleurisy and Effect of a Selective COX-2 Inhibitor", *Advances in Prostaglandin, Thromboxane, and Leukotriene Research* (1995) Vol. 23, pp. 345–347; and Kennedy, Chan, Culp, and Cromlish, "Cloning and Expression of Rat Prostaglandin Endoperoxide Synthase (Cyclooxygenase-2) cDNA", *Biochem. Biophys. Res. Commun.* (1994) Vol. 197, pp. 494–500.

Hence, the differential tissue distribution of COX-1 and COX-2 provides a basis for the development of drugs that are selective COX-2 inhibitors (i.e., specificity for inhibition of COX-2 far exceeds inhibition of COX-1) as antiinflammatory, analgesic, and/or antipyretic agents with minimization of or without the GI and hematologic liabilities from COX-1 inhibition that plague most all currently marketed NSAIDs, most of which inhibit both COX-1 and COX-2, with specificity for COX-1 inhibition greatly exceeding that for COX-2 inhibition, although some have essentially similar inhibitory activity against both COX-1 and COX-2. See, for instance, Meade, Smith, and DeWitt, "Differential Inhibition of Prostaglandin Indoperoxide Synthase (Cyclooxygenase) Isozymes by Aspirin and Other Non-Steroidal Antiinflammatory Drugs", *J. Biol. Chem.*, (1993) Vol. 268, pp. 6610–6614.

Detailed SAR studies have been reported for two general structural classes of selective COX-2 inhibitors (specificity for COX-2 inhibition far exceeds COX-1 inhibition) including certain acidic sulfonamides and certain diarylheterocyclics. The in vivo activities of these selective COX-2 inhibitors validate the concept that selective COX-2 inhibition is antiinflammatory and nonulcerogenic, as discussed in the following journal articles. Gans, Galbraith, Roman, Haber, Kerr, Schmidt, Smith, Hewes, and Ackerman, "Anti-Inflammatory and Safety Profile of DuP 697, a Novel Orally Effective Prostaglandin Synthesis Inhibitor", *J. Pharmacol. Exp. Ther.* (1990) Vol. 254, pp. 180–187; Penning, Talley, Bertenshaw, Carter, Collins, Docter, Graneto, Lee, Malecha, Miyashiro, Rogers, Rogier, Yu, Anderson, Burton, Cogburn, Gregory, Koboldt, Perkins, Seibert, Veenhuizen, Zhang, and Isakson, "Synthesis and Biological Evaluation of the 1,5-Diarylpyrazole Class of Cyclooxygenase-2 Inhibitors: Identification of 4-[5-(4-Methylphenyl)-3-(trifluoromethyl)-1H-pyrazol-1-yl]benzenesulfonamide (SC-58635, Celecoxib)", *J. Med. Chem.* (1997) Vol. 40, pp.1347–1365; Khanna, Weier, Yu, Xu, Koszyk, Collins, Koboldt, Veenhuizen, Perkins, Casler, Masferrer, Zhang, Gregory, Seibert, and Isakson, "1,2-Diarylimidazoles as Potent Cyclooxygenase-2 Selective, and Orally Active Antiinflammatory Agents", *J. Med. Chem.* (1997) Vol. 40, pp. 1634–1647; Khanna, Weier, Yu, Collins, Miyashiro, Koboldt, Veenhuizen, Curie, Siebert, and Isakson, "1,2-Diarylpyrroles as Potent and Selective Inhibitors of Cyclooxygenase-2", *J. Med. Chem.* (1997) Vol. 40, pp. 1619–1633; Tsuji, Nakamura, Konishi, Tojo, Ochi, Senoh, and Matsuo, "Synthesis and Pharmacological Properties of 1,5-Diarylyrazoles and Related Derivatives", *Chem. Pharm. Bull.* (1997) Vol. 45, pp. 987–995; Riendeau, Percival, Boyce, Brideau, Charleson, Cromlish, Ethier, Evans, Falgueyret, Ford-Hutchinson, Gordon, Greig, Gresser, Guay, Kargman, Léger, Mancini, O'Neill, Quellet, Rodger, Thérien, Wang, Webb, Wong, Xu, Young, Zamboni, Prasit, and Chan, "Biochemical and Pharmacological Profile of a Tetrasubstituted Furanone as a Highly Selective COX-2 Inhibitor", *Br. J. Pharmacol.* (1997) Vol. 121, pp.105–117; Roy, Leblanc, Ball, Brideau, Chan, Chauret, Cromlish, Ethier, Gauthier, Gordon, Greig, Guay, Kargman, Lau, O'Neill, Silva, Thérien, Van Staden, Wong, Xu, and Prasit, "A New Series of Selective COX-2 Inhibitors: 5,6-Diarylthiazolo[3,2-b][1,2,4]-triazoles", *Bioorg. Med. Chem. Lett.* (1997) Vol.7, pp.57–62; Thérien, Brideau, Chan, Cromlish, Gauthier, Gordon, Greig, Kargman, Lau, Leblanc, Li, O'Neill, Riendeau, Roy, Wang, Xu, and Prasit, "Synthesis and Biological Evaluation of 5,6-Diarylimidazo[2.1-b]thiazoles as Selective COX-2 Inhibitors", *Bioorg. Med. Chem. Lett.* (1997) Vol.7, pp.47–52; Li, Norton, Reinhard, Anderson, Gregory, Isakson, Koboldt, Masferrer, Perkins, Seibert, Zhang, Zweifel, and Reitz, "Novel Terphenyls as Selective Cyclooxygenase-2 Inhibitors and Orally Active Anti-Inflammatory Agents", *J. Med. Chem.* (1996) Vol. 39, pp. 1846–1856; Li, Anderson, Burton, Cogburn, Collins, Garland, Gregory, Huang, Isakson, Koboldt, Logusch, Norton, Perkins, Reinhard, Seibert, Veenhuizen, Zhang, and Reitz, "1,2-Diarylcyclopentenes as Selective Cyclooxygenase-2 Inhibitors and Orally Active Anti-Inflammatory Agents", *J. Med. Chem.* (1995) Vol. 38, pp. 4570–4578; Reitz, Li, Norton, Reinhard, Huang, Penick, Collins, and Garland, "Novel 1,2-Diarylcyclopentenes are Selective Potent and Orally Active Cyclooxygenase Inhibitors", *Med. Chem. Res.* (1995) Vol. 5, pp. 351–363; Futaki, Yoshikawa, Hamasaka, Arai, Higuchi, Iizuka, and Otomo, "NS-398, A Novel Nonsteroidal Antiinflammatory Drug with Potent Analgesic and Antipyretic Effects, which Causes Minimal Stomach Lesions", *Gen. Phamacol.* (1993) Vol.24, pp.105–110; Wiesenberg-Boetcher, Schweizer, Green, Muller, Maerki, and Pfeilschifter, "The Pharmacological Profile of CGP 28238, A Novel Highly Potent Anti-Inflammatory Compound", *Drugs Exptl Clin Res.* (1989) Vol. XV, pp. 501–509; Futaki, Takahashi, Yokoyama, Arai, Higuchi, and Otomo, "NS-398, A New Anti-Inflammatory Agent, Selectively Inhibits Prostaglandin G/H Synthase/Cyclooxygenase (COX-2) Activity in vitro", *Prostaglandins* (1994) Vol.47, pp.55–59; Klein, Nusing, Pfeilschifter, and Ullrich, "Selective Inhibition of Cyclooxygenase-2", *Biochem. Pharmacol.* (1994) Vol. 48, pp. 1605–1610; Li, Black, Chan, Ford-Hutchinson, Gauthier, Gordon, Guay, Kargman, Lau, Mancini, Quimet, Roy, Vickers, Wong, Young, Zamboni, and Prasit, "Cyclooxygenase-2 Inhibitors. Synthesis and Pharmacological Activities of 5-Methanesulfonamido-1-indanone Derivatives", *J. Med. Chem.* (1995) Vol. 38, pp.4897–8905; Prasit, Black, Chan, Ford-Hutchinson, Gauthier, Gordon, Guay, Kargman, Lau, Li, Mancini, Quimet, Roy, Tagari, Vickers, Wong, Young, and Zamboni, "L-745,337: A Selective Cyclooxygenase-2 Inhibitor", *Med. Chem. Res.* (1995) Vol. 5, pp. 364–374; Tanaka, Shimotori, Makino, Aikawa, Inaba, Yoshida, and Takano, "Pharmacological Studies of the New Antiinflammatory Agent 3-Formylamino-7-methylsulfonylamino-6-phenoxy4H-1-benzopyran4-one. 1st Communication: Antiinflammatory, Analgesic and Other Related Properties", *Arzniem.-Forsch./Drug Res.* (1992) Vol. 42, pp. 935–944; Nakamura, Tsuji, Konishi, Okumura, and Matsuo, "Studies on Anti-Inflammatory Agents. I. Synthesis and Pharmacological Properties of 2'-(phenylthio) methanesulfonamides and Related Derivatives", *Chem. Pharm. Bull.* (1993) Vol. 41, pp. 894–906; Chan, Boyce, Brideau, Ford-Hutchinson, Gordon, Guay, Hill, Li, Mancini, Penneton, Prasit, Rasori, Riendeau, Roy, Tagari, Vickers, Wong, and Rodger, "Pharmacology of a Selective Cyclooxygenase-2 Inhibitor, L-745,337: A Novel Nonsteroidal Anti-Inflammatory Agent with an Ulcerogenic Sparing Effect in Rat and Nonhuman Primate Stomach", *J. Pharmacol. Exp. Ther.* (1995) Vol. 274, pp. 1531–1537; and Graedon and Graedon, "Pills Promise Relief without Ulcers", The Raleigh, North Carolina *News and Observer*, p. 8D (Sep. 13, 1998) which addresses, in general terms, the development of celecoxib, meloxicam, and vioxx as selective COX-2 inhibitors.

Representative acidic sulfonamides and diarylheterocyclics that have been reported as selective COX-2 inhibitors in the journal articles mentioned in the above paragraph are:

Acidic Sulfonamides

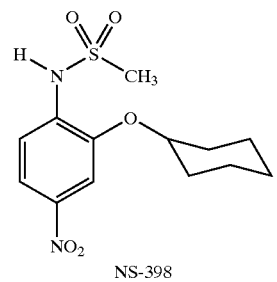
NS-398

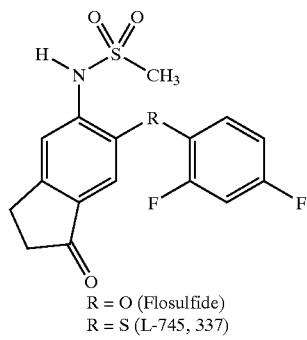
R = O (Flosulfide)
R = S (L-745, 337)

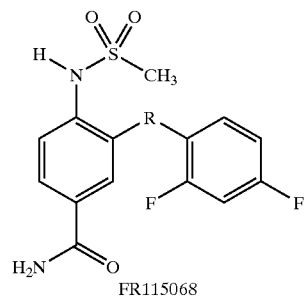
FR115068

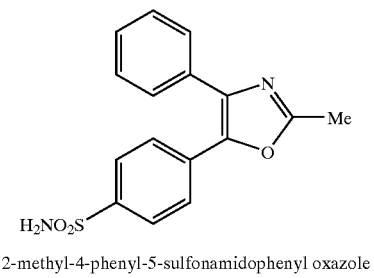
2-methyl-4-phenyl-5-sulfonamidophenyl oxazole

Diarylheterocycles

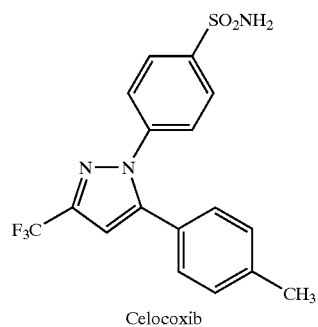
Celocoxib

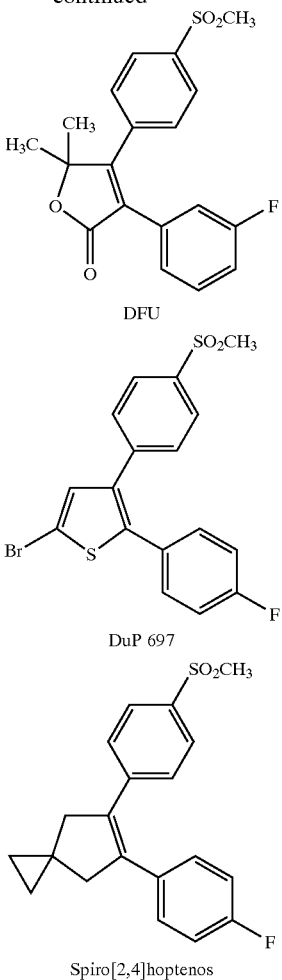

DFU

DuP 697

Spiro[2,4]hoptenos

Although acidic sulfonamides and diarylheterocyclics have been extensively studied as selective COX-2 inhibitors, there are very few reports on converting NSAIDs that are selective COX-1 inhibitors into selective COX-2 inhibitors. See, Black, Bayly, Belley, Chan, Charleson, Denis, Gauthier, Gordon, Guay, Kargman, Lau, Leblanc, Mancini, Quellet, Percival, Roy, Skorey, Tagari, Vickers, Wong, Xu, and Prasit, "From Indomethacin to a Selective COX-2 Inhibitor: Development of Indolalkanoic Acids as Potent and Selective Cyclooxygenase-2 Inhibitors", *Bioorg. Med. Chem. Lett.* (1996) Vol. 6, pp. 725–730; Luong, Miller, Barnett, Chow, Ramesha, and Browner, "Flexibility of the NSAID Binding Site in the Structure of Human Cyclooxygenase-2", *Nature Structural Biol.* (1996) Vol. 3, pp. 927–933; and Kalgutkar, Crews, Rowlinson, Garner, Seibert, and Marnett, "Aspirin-Like Molecules that Covalently Inactivate Cyclooxygenase-2", *Science* (1998, Vol. 280, pp.1268–1270; U.S. Pat. No. 5,681,964 (issued in 1997) to Ashton et al., assignors to the University of Kentucky Research Foundation, which shows conversion of indomethacin (an NSAID) into certain ester derivatives with concomitant reduction of GI irritation (see, FIG. 1 of U.S. Pat. No. 5,681,964 for the structure of the ester derivatives); and U.S. Pat. No. 5,607,966 (Parent) (issued in 1997) and U.S. Pat. No. 5,811,438 (CIP) (issued in 1998), both to Hellberg et al., assignors to Alcon Laboratories, which show conversion of various NSAIDs (such as indomethacin) into certain ester derivatives and amide derivatives (that are useful as antioxidants and inhibitors of 5-lipoxygenase), but which do not address selective COX-2 inhibition.

Moreover, although U.S. Pat. No. 3,285,908 (issued in 1966) and U.S. Pat. No. 3,336,194 (issued in 1967), both to Shen, assignor to Merck & Co., Inc., describe various secondary and tertiary amide derivatives of indomethacin, the patents fail to address COX inhibition, probably because COX inhibition (both COX-1 and COX-2) was undiscovered in the 1960's, and thus fail to recognize that tertiary amide derivatives do not inhibit either COX-1 or COX-2. (Also, see comparison compounds 36 and 37 in Example II below.) However, U.S. Pat. No. 5,436,265 (issued in 1995) to Black et al. and U.S. Pat. No. 5,510,368 (issued in 1996) to Lau et al., both patents assigned to Merck Frosst Canada, Inc., describe, respectively, 1-aroyl-3-indolyl alkanoic acids and N-benzyl-3-indoleacetic acids as COX-2 selective inhibitors.

In the present investigation, the possibility has been explored for designing selective COX-2 inhibitors using as templates various NSAIDs (1) that are selective COX-1 inhibitors or (2) that have essentially the same inhibitory activity for both COX-1 and COX-2. These two kinds of NSAIDs are collectively referred to as NSAIDs that are not selective COX-2 inhibitors.

More particularly, analysis of the human COX-2 crystal structure complexed with zomepirac-derived selective COX-2 inhibitors indicates that the structural basis for selectivity by zomepirac-derived compounds is different from that of diarylheterocyclics. See, Luong et al. mentioned above. Unlike diarylheterocyclics, zomepirac analogs do not utilize the side pocket; instead they breech the constriction at the mouth of the COX active site occupied by Arg106 and Tyr341 and project down the lobby region. The projection into this sterically uncongested region in the COX-2 active site opens the possibility that making a wide range of analogs of COOH-containing drugs, such as analogs of NSAIDs, each with a different pendent functional group replacing the OH or the H of the COOH, would accomplish many purposes related to drug discovery or development. For example, certain pendent groups could improve water-solubility, bioavailability, or pharmacokinetics. Another possibility would be to attach a pendent pharmacophore in order to target a completely different protein leading to compounds with dual pharmacological functions.

Abbott Laboratories and Parke-Davis have attempted the pharmacophore approach. See, respectively, Kolasa, Brooks, Rodriques, Summers, Dellaria, Hulkower, Bouska, Bell, and Carter, "Nonsteroidal Anti-Inflammatory Drugs as Scaffolds fort he Design of 5-Lipoxygenase Inhibitors", *J. Med. Chem.* (1997) Vol. 40, pp. 819–824; and Flynn, Capiris, Cetenko, Connor, Dyer, Kostlan, Niese, Schrier, and Sircar, "Nonsteroidal Antiinflammatory Drug Hydroxamic Acids. Dual Inhibitors of Both Cyclooxygenase and 5-Lipoxygenase", *J. Med. Chem.* (1990) Vol. 33, pp. 2070–2072. Both Kolasa et al. and Flynn et al. reported that replacement of the carboxylic acid group in NSAIDs with a hydroxamic acid moiety or a hydroxyurea moiety provided dual inhibitors of COX and 5-lipoxygenase. Nevertheless, none of the analogs displayed any significant selective COX-2 inhibition, and furthermore the hydroxamates underwent facile hydrolysis.

Additionally, it is interesting to note that sulindac sulfide (an NSAID which contains a COOH moiety as well as a methyl sulfide moiety) is a 40-fold more potent inhibitor against COX-1 than against COX-2. On the other hand, a derivative, namely sulindac sulfone (which contains a COOH moiety as well as a methyl sulfone moiety) does not inhibit either COX-1 or COX-2.

However, nothing in the above-discussed literature suggests that converting a COOH-containing NSAID that is not selective for COX-2 inhibition into an ester derivative or a secondary amide derivative would result in a derivative that is selective for COX-2 inhibition. Thus, it would be desirable to find certain COOH-containing drugs, such as NSAIDs, which are not selective COX-2 inhibitors (either display an inhibition for COX-1 far exceeding inhibition of COX-2 or display essentially the same inhibition for COX-1 and COX-2) that would, when converted into certain derivatives, become selective COX-2 inhibitors (display an inhibition for COX-2 far exceeding inhibition for COX-1), as well as retain the analgesic, antiinflammatory, and/or antipyretic effect of the drug, such as the NSAID, prior to derivatization.

SUMMARY AND OBJECTS OF THE INVENTION

Surprisingly with the present invention, it has been found that derivatization of the carboxylic acid moiety or the pharmaceutically acceptable salt of the moiety of various compounds (for instance, of certain NSAIDs) that are not selective COX-2 inhibitors, such as indomethacin, to ester analogs or to secondary amide analogs creates isozyme specificity for COX-2. Moreover, the resultant ester derivative or secondary amide derivative is not only a selective COX-2 inhibitor, but also retains the analgesic, antiinflammatory, and/or antipyretic effect of the compound, i.e., the NSAID.

Therefore, the present invention provides a method of altering specificity of a cyclooxygenase-inhibiting compound, the method comprising the steps of:
  (a) providing a compound having cyclooxygenase inhibitory activity, the compound having a carboxylic acid moiety or pharmaceutically acceptable salt thereof associated with the cyclooxygenase inhibitory activity and the compound being absent specificity for cyclooxygenase-2 inhibitory activity; and
  (b) altering the specificity of the compound in step (a) from being absent specificity for cyclooxygenase-2 inhibitory activity to having specificity for cyclooxygenase-2 inhibitory activity by converting the compound having the carboxylic acid moiety or pharmaceutically acceptable salt thereof into a derivative having an ester moiety or a secondary amide moiety.

Hence, it is an object of the invention to provide a derivative drug that minimizes or obviates GI irritation. Moreover, it is an advantage of the present invention that the derivative drug is also analgesic, antiinflammatory, and/or antipyretic, absent the concomitant administration of the non-derivatized drug or a pharmaceutically acceptable salt of the non-derivatized drug.

Some of the objects of the invention having been stated above, other objects will become evident as the description proceeds, when taken in connection with the Laboratory Examples as described below.

DETAILED DESCRIPTION OF THE INVENTION

The present invention involves a method for converting a drug into a COX-2 selective inhibitor and also for using that COX-2 selective inhibitor for treating an animal that is a warm-blooded vertebrate. Therefore, the invention concerns mammals and birds.

Contemplated is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, contemplated is the treatment of livestock, including, but not limited to, domesticated swine (pigs and hogs), ruminants, horses, poultry, and the like.

More particularly, a treatment effective amount of an ester derivative or a secondary amide derivative of a carboxylic acid-containing drug, such as a derivative of an NSAID, is administered to the warm-blooded vertebrate animal. Thus, the invention comprises administration of the derivative in concentrations calculated to provide the animal being treated with the appropriate milieu to provide an analgesic, antiinflammatory, or antipyretic effect.

By carboxylic-acid containing drug (such as an NSAID) or COOH-containing drug (such as an NSAID) as used herein in connection with the present invention, it is intended to include pharmaceutically acceptable acid salts of the drug. Thus, for instance, the COOH moiety includes COOM, where M is Na and the like.

The preferred derivative compounds useful in the method of the present invention are secondary amide derivatives and ester derivatives of non-steroidal antiinflammatory drugs having a carboxylic moiety or a pharmaceutically acceptable salt thereof. Various chemical classes of NSAIDs have been identified and are listed in *CRC Handbook of Eicosanoids: Prostaglandins, and Related Lipids, Vol. II, Drugs Acting Via the Eicosanoids*, pages 59–133, CRC Press, Boca Raton, Fla. (1989). Hence, the NSAID may be chosen from a variety of chemical classes including, but not limited to, fenamic acids, such as flufenamic acid, niflumic acid, and mefenamic acid; indoles, such as indomethacin, sulindac, and tolmetin; phenylalkanoic acids, such as suprofen, ketorolac, flurbiprofen, and ibuprofen; and phenylacetic acids, such as diclofenac. Further examples of NSAIDs are listed below:

| aceloferac | etodolic acid | loxoprofen |
| alcofenac | fenbufen | meclofenamate |
| amfenac | fenclofenac | naproxen |
| benoxaprofen | fenclorac | orpanoxin |
| bromfenac | fenoprofen | pirprofen |
| carprofen | fleclozic acid | pranoprofen |
| clidanac | indoprofen | tolfenamic acid |
| diflunisal | isofezolac | zaltoprofen |
| efenamic acid | ketoprofen | zomopirac |

More specifically, preferred ester derivatives and secondary amide derivatives useful in the present invention include, but are not limited to, ester derivatives and secondary amide derivatives of the following COOH-containing NSAIDs: 6-methoxy-α-methyl-2-naphthylacetic acid (and its Na acid salt form known as naproxen), meclofenamic acid, and diclofenac, with ester derivatives and secondary amide derivatives of indomethacin being preferred. Also, the ester derivatives and the secondary amide derivatives of indomethacin, where the Cl at the 4-position of the benzoyl moiety is replaced with Br or F, should work in the present invention. Even more preferred are the secondary amide derivatives of indomethacin including, but not limited to, indomethacin-N-methyl amide, indomethacin-N-ethan-2-ol amide, indomethacin-N-octyl amide, indomethacin-N-nonyl amide, indomethacin-N-(2-methylbenzyl) amide, indomethacin-N-(4-methylbenzyl) amide, indomethacin-N-((R)-,4-dimethylbenzyl) amide, indomethacin-N-((S)-,4-dimethylbenzyl) amide, indomethacin-N-(2-phenethyl) amide, indomethacin-N-(4-fluorophenyl) amide, indomethacin-N-(4-chlorophenyl) amide, indomethacin-N-(4-acetamidophenyl) amide, indomethacin-N-(4-methylmercapto)phenyl amide, indomethacin-N-(3-methylmercaptophenyl) amide, indomethacin-N-(4-methoxyphenyl) amide, indomethacin-N-(3-ethoxyphenyl) amide, indomethacin-N-(3,4,5-trimethoxyphenyl) amide, indomethacin-N-(3-pyridyl) amide, indomethacin-N-5-((2-chloro)pyridyl) amide, indomethacin-N-5-((1-ethyl) pyrazolo) amide, indomethacin-N-(3-chloropropyl) amide, indomethacin-N-methoxycarbonylmethyl amide, indomethacin-N-2-(2-L-methoxycarbonylethyl) amide, indomethacin-N-2-(2-D-methoxycarbonylethyl) amide, indomethacin-N-(4-methoxycarbonylbenzyl) amide, indomethacin-N-(4-methoxycarbonyl methylphenyl) amide, indomethacin-N-(2-pyrazinyl) amide, indomethacin-N-2-(4-methylthiazolyl) amide, indomethacin-N-(4-biphenyl) amide, and combinations thereof.

The ester derivative or the secondary amide derivative may be administered to the animal as a suppository or as a supplement to fluids that are administered internally or parenterally, for instance nutriment fluids such as intervenous sucrose solutions. Furthermore, intraoral (such as buccal or sublingual) administration or transdermal (such as with a skin patch) administration to the animal is also contemplated. A good discussion of intraoral administration can be seen in U.S. Pat. No. 4,229,447 issued Oct. 21, 1980 to Porter and U.S. Pat. No. 5,504,086 issued Apr. 2, 1996 to Ellinwood and Gupta. A good discussion of transdermal administration can be seen in U.S. Pat. No. 5,016,652 issued May 21, 1991 to Rose and Jarvik.

Additionally, administration to the animal may be by various oral methods, for instance as a tablet, capsule, or powder (crystalline form) that is swallowed. Also, oral administration may include that the ester derivative or the secondary amide derivative is admixed in a carrier fluid appropriate therefor so that it is administered as a liquid (solution or suspension) that is drunk. When the derivative is admixed in a carrier fluid, appropriate fluids include, but are not limited to, water, rehydration solutions (i.e., water with electrolytes such as potassium citrate and sodium chloride, for instance the solution available under the trade name RESOL® from Wyeth Laboratories), nutritional fluids (i.e., milk, fruit juice), and combinations thereof. Thus, the oral administration may be as a component of the diet, such as human food, animal feed, and combinations thereof.

In addition to oral administration such as by way of the mouth, contemplated also is administration of a solution or suspension to the esophagus, stomach, and/or duodenum, such as by gavage, i.e., by way of a feeding tube. Gavage type of administration is useful for when the animal is very ill and can no longer swallow food, medicine, et cetera, by mouth.

Hence, it is also contemplated that additional ingredients, such as various excipients, carriers, surfactants, nutriments, and the like, as well as various medicaments, other than the ester derivative or other than the secondary amide derivative, or combinations thereof, may be present together with the derivative, whatever the form that the derivative is in. Medicaments other than an ester derivative or a secondary amide derivative may include, but are not limited to, osmolytic polyols and osmolytic amino acids (i.e., myo-inositol, sorbitol, glycine, alanine, glutamine, glutamate, aspartate, proline, and taurine), cardiotonics (i.e., glycocyamine), analgesics, antibiotics, electrolytes (i.e., organic or mineral electrolytes such as salts), and combinations thereof.

A suitable dosing amount of ester derivative or secondary amide derivative for administration to the animal should range from about 0.5 mg to about 7.0 mg per kg of body weight of the animal per day, more preferably from about 1.5 mg to about 6.0 mg per kg of body weight of the animal per day, and even more preferably from about 2.0 mg to about 5.0 mg per kilogram of body weight of the animal per day. Administration may be one or more times per day to achieve the total desired daily dose. Of course, the amount can vary depending on the severity of the illness and/or the age of the animal.

The present invention indicates that carboxylic acid-containing compounds that are not COX-2 selective inhibitors, such as the NSAID known as indomethacin, when converted into esters or into secondary amides, results in isozyme specificity for COX-2 and thus presents an efficient strategy for the generation of potent and selective COX-2 inhibitors. The below-discussed extensive SAR study conducted with indomethacin suggests that a variety of ester substituents are tolerated for replacing the H in the COOH moiety of indomethacin and that a variety of secondary amide substituents are tolerated for replacing the OH in the COOH moiety of indomethacin, and these resultant derivatives are as potent and selective as COX-2 inhibitors as are the diarylheterocyclics discussed above. Thus, this strategy has great potential in the development of nonulcerogenic antiinflammatory agents.

LABORATORY EXAMPLES

The following is noted in connection with the materials and procedures below.

The esters that were made and their selective COX-2 inhibition properties are listed in the Table 1 below. A total of 29 analogs (29 ester derivatives) of indomethacin were prepared. The amides that were made and their selective COX-2 inhibition properties are listed in Table 2 below. A total of 31 analogs (31 amide derivatives) of indomethacin were prepared.

Most of the NSAID esters were prepared by treatment of the NSAID with the appropriate alcohol or phenol in the presence of DCC and DMAP, described herein as Method B (details on ester preparation by Method A are given below). The reaction scheme for ester preparation as per Method B and the reaction scheme for amide preparation were, respectively, as follows:

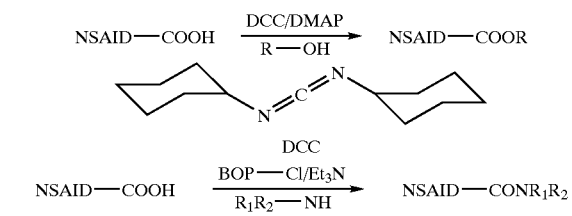

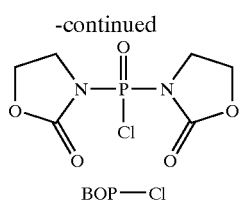

BOP—Cl

Various nitrogen-containing substituents (i.e., amines) that replaced the OH of the COOH, in order to create an amide, included aminoalkyl, aminoaryl, aminoarylalkyl, aminoethers, or aminopyridinyl moieties as part of the nitrogen-containing substituent. The most potent amide analogs in the indomethacin derivative series displayed $IC_{50}$ values for inhibition of purified human COX-2 in the low nanomolar range with COX-2 selectivity ratios ranging from >1000–4000. Well established methodology was utilized in the synthesis of amide derivatives of indomethacin by treatment of the indomethacin with an appropriate amine (designated as R) utilizing BOP-Cl as the carboxylic acid activator to replace the OH of the COOH with R and create an amide. If R was a primary amine, the resultant derivative was a secondary amide, and if R was a secondary amine, the resultant derivative was a tertiary amide.

More specifically, a reaction mixture containing indomethacin (300 mg, 0.84 mmol) and BOP-Cl (218 mg, 0.84 mmol) in 5 mL of anhydrous $CH_2Cl_2$ was treated with $Et_3N$ (167 mg, 0.84 mmol) and allowed to stir at rt for 10 minutes. The mixture was then treated with the appropriate amine (0.94 mmol) designated as R and stirred overnight at rt. Following dilution with $CH_2Cl_2$ (30 mL), the resultant solution was washed with water (2×25 mL), 3 N NaOH (2×25 mL), water (2×30 mL), dried (in the presence of $MgSO_4$), filtered, and the solvent concentrated in vacuo. The crude amide was purified by chromatography on silica gel or recrystallization in the appropriate solvent.

$IC_{50}$ values for the inhibition of purified human COX-2 or ovine COX-1 by test compounds were determined by the TLC assay discussed below. Ovine COX-1 was used because it is very easy to isolate and to purify the enzyme from sheep seminal vesicles, whereas human COX-1 is normally obtained by over expression in an insect cell system and is very difficult to handle and especially to purify. COX-1 from sheep is >90% similar to COX-1 from humans. Finally, inhibition of COX-1 from these two sources by NSAIDs has been reported in the published literature and the $IC_{50}$ values are similar, suggesting no dramatic active site differences. COX-1 was purified from ram seminal vesicles obtained from Oxford Biomedical Research, Inc. (Oxford, Mich.). The specific activity of the protein was 20 ($\mu MO_2$/minute)/mg, and the percentage of holoprotein was 13.5%. Samples of human COX-2 (1.62 $\mu g/\mu l$) were obtained by expression of insect cell cloned human COX-2 carried on baculovirus vectors, followed by purification. The enzymes obtained after purification were apo (i.e., they lacked the hemprosthetic group). They were reconstituted with hematin purchased from Sigma Chemical Co. (St. Louis, Mo.) in the assays to render them to their natural states which is holo (i.e., natural COX-1 and natural COX-2 contain the hemprosthetic group) so that the inhibition by test compounds had physiological relevance.

HoloCOX-2 (66 nM) or holoCOX-1 (44 nM) in 100 mM Tris-HCl, pH 8.0 containing 500 $\mu M$ phenol was treated with several concentrations of indomethacin, an ester derivative of indomethacin, or an amide derivative of indomethacin at 25° C. for 20 minutes. Since the recombinant COX-2 had a lower specific activity than the ovine COX-1, the protein concentrations were adjusted such that the percentages of total products obtained following catalysis of arachidonic acid (purchased from Nu Chek Prep, Elysian, Minn.) by the two isoforms were comparable. More specifically, time- and concentration-dependent inhibition of cyclooxygenase activity for ovine COX-1 (44 nM) and human COX-2 (66 nM) using the TLC assay was determined as follows. Reaction mixtures of 200 $\mu L$ contained hematin-reconstituted protein in 100 mM Tris-HCl, pH 8.0, 500 $\mu M$ phenol, and [1-$^{14}$C]-arachidonic acid (50 $\mu M$, ~55–57 mCi/mmol). For the time-dependent inhibition assay, hematin-reconstituted COX-1 (44 nM) or COX-2 (66 nM) was preincubated at rt for 20 minutes with varying inhibitor concentrations in DMSO followed by the addition of [1-$^{14}$C]-arachidonic acid (50 $\mu M$) for 30 seconds at 37° C. [1-$^{14}$C]-arachidonic acid (~55–57 mCi/mmol) was purchased from New England Nuclear, Dupont, or American Radiolabeled Chemicals (St. Louis, Mo.).

Reactions were terminated by solvent extraction in $Et_2O$/$CH_3OH$/1 M citrate, pH 4.0 (30:4:1). The phases were separated by centrifugation at 2000 g-force for 2 minutes and the organic phase was spotted on a TLC plate (obtained from J. T. Baker, Phillipsburg, N.J.). The plate was developed in EtOAc/$CH_2Cl_2$/glacial AcOH (75:25:1) at 4° C. Radiolabeled prostanoid products were quantitatively determined with a radioactivity scanner (obtained from Bioscan, Inc., Washington, D.C.). The percentage of total products observed at different inhibitor concentrations was divided by the percentage of products observed for protein samples preincubated for the same time with DMSO.

Control experiments in the absence of indomethacin indicated ~25–30% conversion of fatty acid substrate to products, which was sufficient for assessing the inhibitory properties of all test compounds. Under these conditions, indomethacin displayed selective time- and concentration-dependent inhibition of COX-1 (i.e., $IC_{50}$ (COX-1)~0.050 $\mu M$; $IC_{50}$ (COX-2)~0.75 $\mu M$), whereas the ester derivatives and the secondary amide derivatives displayed selective COX-2 inhibition but the tertiary amide derivatives did not inhibit either COX-1 or COX-2 (i.e., measurement of COX-2 was stopped at an extremely high $IC_{50}$ and still >80% COX-2 activity remained). Also, the following is noted for NS-398 and 2-methyl4-phenyl-5-sulfoamidophenyl oxazole, which are two of the above-mentioned acidic sulfonamides, namely, NS-398: $IC_{50}$ (COX-2)~0.12 $\mu M$; $IC_{50}$ (COX-1)>66 $\mu M$; and 2-methyl4-phenyl-5-sulfoamidophenyi oxazole: $IC_{50}$ (COX-2)~0.06 PM; $IC_{50}$ (COX-1)>66 $\mu M$.

For certain comparison tests, inhibition of COX-2 activity in activated murine RAW264.7 cells was determined as follows. Low passage number murine RAW264.7 cells were grown in DMEM containing 10% heat-inactivated FBS. Cells (6.2×10$^6$ cells/T25 flask) were activated with 500 ng/mL LPS and 10 units/mL IFN-g in serum-free DMEM for 7 hours. Vehicle (DMSO) or inhibitor in DMSO (0 to 1 $\mu M$) was added for 30 minutes at 37° C. Inhibition of exogenous arachidonic acid metabolism or inhibition of $PGD_2$ synthesis was determined by incubating the respective cells with 20 $\mu M$ $^{14}$C-AA for 15 minutes at 25° C. Aliquots (200 $\mu L$) were removed into termination solution and total products were quantitatively determined by the TLC assay.

Melting points were determined using a Gallenkamp melting point apparatus and were uncorrected. Chemical yields were unoptimized specific examples of one preparation. NSAIDs (i.e., indomethacin) were purchased from Sigma (St. Louis, Mo.). All other chemicals were purchased from Aldrich (Milwaukee, Wis.). Methylene chloride was purchased as anhydrous from Aldrich and was used as received. All other solvents were HPLC grade. Analytical TLC (Analtech uniplates™) was used to follow the course of reactions. Silica gel (Fisher, 60–100 mesh) was used for column chromatography. $^1$H NMR and $^{13}$C NMR spectra in $CDCl_3$ were recorded on a Bruker WP-360 spectrometer or an AM400 spectrometer. Chemical shifts were expressed in parts per million (ppm) relative to tetramethylsilane as an internal standard. Spin multiplicities were reported as s (singlet), d (doublet), dd (doublet of doublets), t (triplet), q (quartet), and m (multiplet). Coupling constants (J) were reported in hertz (Hz).

Example I

Derivatives with Ester Moiety. The following ester derivatives of indomethacin, designated as compounds 2 through 29, were made.

Procedure for the Esterification of NSAIDs. Method A: To a reaction mixture containing the appropriate NSAID (1 mmol) in 40 mL of the desired alcohol was added 2 drops of concentrated HCl and this mixture was heated under reflux for 2 hours. The reaction mixture was allowed to attain rt and the solvent was concentrated in vacuo. The residue was diluted with water and extracted with $Et_2O$ (3×10 mL). The combined organic solution was washed with 1 N NaOH (2×20 mL), water (~50 mL), dried (in the presence of $MgSO_4$), filtered, and concentrated in vacuo. The residue was chromatographed on silica gel and eluted with the appropriate solvent.

Indomethacin methyl ester (compound 2) was obtained as a fluffy white solid (251 mg, 67%) upon chromatography on silica gel (EtOAc:hexanes; 20:80) followed by recrystallization from $Et_2O$. mp=94–96° C.; $^1$H NMR ($CDCl_3$) δ 7.65–7.68 (d, 2H, J=8.3 Hz, ArH), 7.45–7.48 (d, 2H, J=8.4 Hz, ArH), 6.95–6.96 (d, 1H, J=2.2 Hz, ArH), 6.84–6.87 (d, 1H, J=9.0 Hz, ArH), 6.64–6.68 (dd, 1H, J=9.0 Hz and 2.4 Hz, ArH), 3.84 (s, 3H, $CH_3$), 3.72 (s, 3H, $CH_3$), 3.67 (s, 2H, $CH_2$), 2.38 (s, 3H, $CH_3$).

Indomethacin ethyl ester (compound 3) was obtained as a fluffy white solid (300 mg, 81%) upon chromatography on silica gel (EtOAc:hexanes; 10:90) followed by recrystallization from $Et_2O$. mp=100–101° C.; $^1$H NMR ($CDCl_3$) δ 7.65–7.67 (d, 2H, J=8.4 Hz, ArH), 7.45–7.48 (d, 2H, J=8.4 Hz, ArH), 6.96–6.97 (d, 1H, J=2.4 Hz, ArH), 6.85–6.88 (d, 1H, J=9.0 Hz, ArH), 6.64–6.68 (dd, 1H, J=9.0 Hz and 2.5 Hz, ArH), 4.12–4.19 (q, 2H, J=7.1 Hz, $CH_2$), 3.83 (s, 3H, $CH_3$), 3.65 (s, 2H, $CH_2$), 2.38 (s, 3H, $CH_3$), 1.24–1.28 (t, 3 H, J=7.1 Hz, $CH_3$).

Indomethacin propyl ester (compound 4) was obtained upon chromatography on silica gel (EtOAc:hexanes; 10:90) as a yellow gum that eventually solidified upon freezing (321 mg, 83%). mp=74–76° C.; $^1$H NMR ($CDCl_3$) δ 7.64–7.67 (d, 2H, J=8.5 Hz, ArH), 7.44–7.48 (d, 2H, J=8.5 Hz, ArH), 6.96–6.97 (d, 1H, J=2.5 Hz, ArH), 6.85–6.88 (d, 1H, J 8.9 Hz, ArH), 6.64–6.68 (dd, 1H, J=8.9 Hz and 2.5 Hz, ArH), 4.03–4.08 (t, 2H, J=6.7 Hz, $CH_2$), 3.83 (s, 3H, $CH_3$), 3.66 (s, 2H, $CH_2$), 2.38 (s, 3H, $CH_3$), 1.58–1.70 (m, 2H, $CH_2$), 0.88–0.93 (t, 3H, J=7.5 Hz, $CH_3$)

Indomethacin isopropyl ester (compound 5) was obtained as a white crystalline solid (325 mg, 84%) upon chromatography on silica gel (EtOAc:hexanes; 10:90) followed by recrsytallization with $Et_2O$. mp=73–75° C.; $^1$H NMR ($CDCl_3$) δ 7.63–7.67 (d, 2H, J=8.5 Hz, ArH), 7.45–7.48 (d, 2H, J=8.4 Hz, ArH), 6.96–6.97 (d, 1H, J=2.5 Hz, ArH), 6.86–6.89 (d, 1H, J=8.9 Hz, ArH), 6.64–6.68 (dd, 1H, J=8.9 Hz and 2.5 Hz, ArH), 4.99–5.03 (m, 1H, CH), 3.83(s, 3H, $CH_3$), 3.62 (s, 2H, $CH_2$), 2.37 (s, 3H, $CH_3$), 1.22–1.24 (d, 6H, 2 $CH_3$).

Indomethacin butyl ester (compound 6) was obtained upon chromatography on silica gel (EtOAc:hexanes; 10:90) as a yellow gum that eventually solidified upon freezing (354 mg, 88%). mp=77–78° C.; $^1$H NMR ($CDCl_3$) δ 7.63–7.68 (d, 2H, J=8.7 Hz, ArH), 7.44–7.49 (d, 2H, J=8.8 Hz, ArH), 6.96–6.97 (d, 1H, J=2.5 Hz, ArH), 6.85–6.88 (d, 1H, J=9.0 Hz, ArH), 6.64–6.68 (dd, 1H, J=9.0 Hz and 2.5 Hz, ArH), 4.07–4.12 (t, 2H, J=6.6 Hz, $CH_2$), 3.83 (s, 3H, $CH_3$), 3.65 (s, 2H, $CH_2$), 2.38 (s, 3H, $CH_3$), 1.56–1.65 (m, 2H, $CH_2$), 1.30–1.40 (m, 2H, $CH_2$), 0.87–0.92 (t, 3H, J=7.3 Hz, $CH_3$).

Procedure for the Esterification of NSAIDs. Method B: A reaction mixture containing indomethacin (300 mg, 0.84 mmol) in 6 mL of anhydrous $CH_2Cl_2$ was treated with dicyclohexylcarbodiimide (192 mg, 0.92 mmol), 4-dimethylamino pyridine (10 mg, 84 μmol), and the appropriate alcohol (0.92 mmol). After stirring at rt for 5 hours, the reaction mixture was filtered and the filtrate was concentrated in vacuo. The residue was diluted with water (~30 mL) and extracted with EtOAc (2×30 mL). The combined organic solution was washed with 5% AcOH (2×30 mL), 1 N NaOH (2×30 mL), water (~100 mL), dried (in the presence of $MgSO_4$), filtered, and the solvent was concentrated in vacuo. The crude product was purified by chromatography on silica gel.

Indomethacin pentyl ester (compound 7) was obtained upon chromatography on silica gel (EtOAc:hexanes; 20:80) as a yellow gum that eventually solidified upon freezing (326 mg, 91%). mp=80–81° C.; $^1$H NMR ($CDCl_3$) δ 7.63–7.67 (d, 2H, J=8.5 Hz, ArH), 7.45–7.48 (d, 2H, J=9.0 Hz, ArH), 6.96–6.97 (d, 1H, J=2.5 Hz, ArH), 6.85–6.88 (d, 1H, J=9.0 Hz, ArH), 6.64–6.68 (dd, 1H, J=9.0 Hz and 2.5 Hz, ArH), 4.06–4.11 (t, 2H, J=6.7 Hz, $CH_2$), 3.83 (s, 3H, $CH_3$), 3.65 (s, 2H, $CH_2$), 2.38 (s, 3H, $CH_3$), 1.56–1.63 (m, 2H, $CH_2$), 1.20–1.30 (m, 4H, $CH_2$), 0.83–0.88 (t, 3H, J=6.8 Hz, $CH_3$).

Indomethacin hexyl ester (compound 8) was obtained upon chromatography on silica gel (EtOAc:hexanes; 10:90) as a yellow gum that eventually solidified upon freezing (290 mg, 79%). mp=62–64° C.; $^1$H NMR ($CDCl_3$) δ 7.64–7.67 (d, 2H, J=8.5 Hz, ArH), 7.45–7.48 (d, 2H, J=9.0 ArH), 6.96–6.97 (d, 1H, J=2.5 Hz, ArH), 6.84–6.87 (d, 1H, J=9.0 Hz, ArH), 6.64–6.67 (dd, 1H, J=9.0 Hz and 2.5 Hz, ArH), 4.06–4.11 (t, 2H, J=6.7 Hz, $CH_2$), 3.83 (s, 3H, $CH_3$), 3.65 (s, 2H, $CH_2$), 2.38 (s, 3H, $CH_3$), 1.58–1.53 (m, 2H, $CH_2$), 1.25–1.33 (m, 6H, $CH_2$), 0.83–0.87 (t, 3H, J=6.8 Hz, $CH_3$)

Indomethacin cyclohexyl ester (compound 9) was obtained upon chromatography on silica gel (EtOAc:hexanes; 10:90) as a fluffy white solid (455 mg, 93%). mp=129–130° C.; $^1$H NMR ($CDCl_3$) δ 7.63–7.67 (d, 2H, J=8.7 Hz, ArH), 7.45–7.47 (d, 2H, J=8.5 Hz, ArH), 6.97–6.98 (d, 1H, J=2.5 Hz, ArH), 6.86–6.89 (d, 1H, J=9.0 Hz, ArH), 6.64–6.68 (dd, 1H, J=9.0 Hz and 2.5 Hz, ArH), 4.76–4.78 (m, 1H, CH), 3.83 (s, 3H, $CH_3$), 3.63 (s, 2H, $CH_2$), 2.37 (s, 3H, $CH_3$), 1.79–1.83 (m, 2H, $CH_2$), 1.65–1.68 (m, 2H, $CH_2$), 1.28–1.53 (m, 6H, $CH_2$).

Indomethacin cyclohexylethyl ester (compound 10) was obtained upon chromatography on silica gel (EtOAc:hexanes; 10:90) as a yellow solid (390 mg, 96%). mp=94–95° C.; $^1$H NMR ($CDCl_3$) δ 7.64–7.67 (d, 2H, J=8.5 Hz, ArH), 7.45–7.48 (d, 2H, J=8.5 Hz, ArH), 6.96–6.97 (d, 1H, J=2.4 Hz, ArH), 6.84–6.87 (d, 1H, J=9.0 Hz, ArH), 6.64–6.68 (dd, 1H, J=9.0 Hz and 2.5 Hz, ArH), 4.10–4.15 (t, 2H, J=6.8 Hz, CH$_2$), 3.83 (s, 3H, CH$_3$), 3.65 (s, 2H, CH$_2$), 2.38 (s, 3H, CH$_3$), 1.62–1.65 (m, 5H, CH$_2$ and CH), 1.46–1.52 (q, 2H, CH$_2$), 1.09–1.27 (m, 4H, CH$_2$), 0.84–0.91 (m, 2H, CH$_2$).

Indomethacin heptyl ester (compound 11) was obtained upon chromatography on silica gel (EtOAc:hexanes; 5:95) as a yellow solid (342 mg, 89%). mp=70–72° C.; $^1$H NMR (CDCl$_3$) δ 7.64–7.67 (d, 2H, J=8.5 Hz, ArH), 7.45–7.48 (d, 2H, J=8.4 Hz, ArH), 6.96–6.97 (d, 1H, J=2.4 Hz, ArH), 6.85–6.88 (d, 1H, J=9.0 Hz, ArH), 6.64–6.67 (dd, 1H, J=9.0 Hz and 2.5 Hz, ArH), 4.06–4.11 (t, 2H, J=6.7 Hz, CH$_2$), 3.83 (s, 3H, CH$_3$), 3.65 (s, 2H, CH$_2$), 2.38 (s, 3H, CH$_3$), 1.56–1.63 (m, 2H, CH$_2$), 1.23–1.27 (m, 8H, CH$_2$), 0.83–0.88 (t, 3H, J=7.0Hz, CH$_3$).

Indomethacin butoxyethyl ester (compound 12) was obtained upon chromatography on silica gel (EtOAc:hexanes; 10:90) as a yellow oil which solidified upon freezing (368 mg, 96%). mp=58–59° C.; $^1$H NMR (CDCl$_3$) δ 7.65–7.68 (dd, 2H, J=6.7 Hz and 1.9 Hz, ArH), 7.45–7.48 (dd, 2H, J=6.8 Hz and 2.0 Hz, ArH), 6.96–6.97 (d, 1H, J=2.5 Hz, ArH), 6.85–6.88 (d, 1H, J=9.0 Hz, ArH), 6.64–6.68 (dd, 1H, J=9.1 Hz and 2.5 Hz, ArH), 4.24–4.27 (t, 2H, J=4.8 Hz, CH$_2$), 3.84 (s, 3H, CH$_3$), 3.70 (s, 2H, CH$_2$), 3.60–3.64 (t, 2H, J=4.7 Hz, CH$_2$), 3.40–3.45 (t, 2H, J=6.6 Hz, CH$_2$), 2.38 (s, 3H, CH$_3$), 1.50–1.56 (m, 2H, CH$_2$), 1.26–1.37 (m, 2H, CH$_2$), 0.88–0.92 (t, 3H, J=7.3 Hz, CH$_3$).

Indomethacin trans-hept-2-enyl ester (compound 13) was obtained upon chromatography on silica gel (EtOAc:hexanes; 10:90) as a yellow oil which solidified upon freezing (380 mg, 97%). mp=76–78° C.; $^1$H NMR (CDCl$_3$) δ 7.64–7.67 (d, 2H, J=8.5,Hz, ArH), 7.45–7.48 (d, 2H, J=8.5Hz, ArH), 6.95–6.96 (d, 1H, J=2.4 Hz, ArH), 6.85–6.88 (d, 1H, J=9.0 Hz, ArH), 6.64–6.68 (dd, 1H, J=9.0 Hz and 2.5 Hz, ArH), 5.69–5.77 (m, 1H, olefinic H), 5.49–5.59 (m, 1H, olefinic H), 4.53–4.55 (d, 2H, J=6.5 Hz, CH$_2$), 3.83 (s, 3H, CH$_3$), 3.66 (s, 2H, CH$_2$), 2.38 (s, 3H, CH$_3$), 2.00–2.06 (m, 2H, CH$_2$), 1.23–1.36 (m, 4 H CH$_2$), 0.85–0.90 (t, 3H, J=7.0 Hz, CH$_3$).

Indomethacin hept-2-ynyl ester (compound 14) was obtained upon chromatography on silica gel (EtOAc:hexanes; 5:95) as a yellow oil which solidified upon freezing (317 mg, 81%). mp=77–79° C.; $^1$H NMR (CDCl$_3$) δ 7.65–7.67 (d, 2H, J=8.4 Hz, ArH), 7.45–7.48 (d, 2H, J=8.4 Hz, ArH), 6.96–6.97 (d, 1H, J=2.4 Hz, ArH), 6.85–6.88 (d, 1H, J=9.0 Hz, ArH), 6.64–6.68 (dd, 1H, J=9.0 Hz and 2.4 Hz, ArH), 4.68–4.70 (t, 2H, J=2.0 Hz, CH$_2$), 3.84 (s, 3H, CH$_3$), 3.70 (s, 2H, CH$_2$), 2.38 (s, 3H, CH$_3$), 2.18–2.23 (m, 2H, CH$_2$), 1.31–1.52 (m, 4H, CH$_2$), 0.87–0.91 (t, 3H, J=6.9 Hz, CH$_3$).

Indomethacin 2-(hept-4-ynyl) ester (compound 15) was obtained upon chromatography on silica gel (EtOAc:hexanes; 5:95) as a yellow oil (329 mg, 84%). mp=69–71° C.; $^1$H NMR (CDCl$_3$) δ 7.64–7.67 (d, 2H, J=8.5 Hz, ArH), 7.45–7.48 (d, 2H, J=8.5 Hz, ArH), 6.96–6.97 (d, 1H, J=2.4 Hz, ArH), 6.86–6.89 (d, 1H, J=9.0 Hz, ArH), 6.64–6.68 (dd, 1H, J=9.0 Hz and 2.4 Hz, ArH), 4.94–5.02 (m, 1H, CH), 3.83 (s, 3H, CH$_3$), 3.64 (s, 2H, CH$_2$), 2.33–2.47 (m merged with a s, 5H, CH$_2$ and CH$_3$), 2.04–2.13 (m, 2H, CH$_2$), 1.29–1.31 (d, 3H, J=6.3 Hz, CH$_3$), 1.04–1.09 (t, 3H, J=7.4 Hz, CH$_3$).

Indomethacin octyl ester (compound 16) was obtained upon chromatography on silica gel (EtOAc:hexanes; 5:95) as a yellow gum which solidified upon freezing (355 mg, 90%). mp=56–57° C.; $^1$H NMR (CDCl$_3$) δ 7.64–7.67 (d, 2H, J=8.5 Hz, ArH), 7.45–7.48 (d, 2H, J=8.4 Hz, ArH), 6.96–6.97 (d, 1H, J=2.4 Hz, ArH), 6.85–6.87 (d, 1H, J=9.0 Hz, ArH), 6.64–6.67 (dd, 1H, J=9.0Hz and 2.5Hz, ArH), 4.06–4.10 (t, 2H, J=6.6Hz, CH$_2$), 3.83 (s, 3H, CH$_3$), 3.65 (s, 2H, CH$_2$), 2.38 (s, 3H, CH$_3$), 1.58–1.62 (m, 2H, CH$_2$), 1.23–1.24 (m, 10H, CH$_2$), 0.84–0.88 (t, 3H, J=7.1 Hz, CH$_3$).

Indomethacin phenyl ester (compound 17) was obtained upon chromatography on silica gel (EtOAc:hexanes; 20:80) as a crystalline white solid (155 mg, 43%). mp=138–140° C.; $^1$H NMR (CDCl$_3$) δ 7.66–7.68 (d, 2H, J=8.4 Hz, ArH), 7.45–7.48 (d, 2H, J=8.5 Hz, ArH), 7.33–7.38 (m, 2H, ArH), 7.03–7.06 (m, 3H, ArH), 6.87–6.90 (d, 1H, J=9.0 Hz, ArH), 6.67–6.71 (dd, 1 H, J=9.0 Hz and 2.5 Hz, ArH), 3.90 (s, 2H, CH$_2$), 3.83 (s, 3H, CH$_3$), 2.45 (s, 3H, CH$_3$).

Indomethacin 3,5-dimethylphenyl ester (compound 18) was obtained upon chromatography on silica gel (EtOAc:hexanes; 20:80) as a yellow oil that solidified upon freezing (219 mg, 54%). mp=143–145° C.; $^1$H NMR (CDCl$_3$) δ 7.67–7.69 (d, 2H, J=8.3 Hz, ArH), 7.46–7.49 (d, 2H, J=8.4 Hz, ArH), 7.05–7.06 (d, 1H, J=2.4 Hz, ArH), 6.89–6.92 (d, 1H, J=9.0 Hz, ArH), 6.85 (s, 1H, ArH), 6.67–6.71 (m, 3H, ArH), 3.88 (s, 2H, CH$_2$), 3.84 (s, 3H, CH$_3$), 2.45 (s, 3H, CH$_3$), 2.29 (s, 6H, 2 CH$_3$).

Indomethacin 4-methylmercaptophenyl ester (compound 19) was obtained upon chromatography on silica gel (EtOAc:hexanes; 20:80) as a yellow oil that solidified upon freezing (307 mg, 76%). mp=132–133° C.; $^1$H NMR (CDCl$_3$) δ 7.66–7.69 (d, 2H, J=8.4 Hz, ArH), 7.46–7.49 (d, 2H, J=8.5 Hz, ArH), 7.22–7.23 (d, 1H, J=2.4 Hz, ArH), 7.04–7.05 (d, 1H, J=2.4 Hz, ArH), 6.97–7.00 (d, 2H, J=8.6 Hz, ArH), 6.87–6.90 (d, 1H, J=9.0 Hz, ArH), 6.67–6.71 (dd, 1H, J=9.0 Hz and 2.5 Hz, ArH), 3.89 (s, 2H, CH$_2$), 3.83 (s, 3H, CH$_3$), 2.46 (s, 3H, CH$_3$), 2.45 (s, 3H, CH$_3$).

Indomethacin 2-methylmercaptophenyl ester (compound 20) was obtained upon chromatography on silica gel (EtOAc:hexanes; 15:85) as a off-white solid (335 mg, 85%). mp=147–148° C.: $^1$H NMR (CDCl$_3$) δ 7.67–7.70 (dd, 2H, J=6.5 Hz and 1.8 Hz, ArH), 7.46–7.49 (dd, 2H, J=6.8 Hz and 1.9 Hz, ArH), 7.17–7.26 (m, 3H, ArH), 7.02–7.05 (dd, 1H, J=7.7 Hz and 1.2 Hz, ArH), 6.90–6.93 (d, 1H, J=8.9 Hz, ArH), 6.68–6.72 (dd, 1H, J=9.1 Hz and 2.5 Hz, ArH), 3.98 (s, 2H, CH$_2$), 3.86 (s, 3H, CH$_3$), 2.47 (s, 3H, CH$_3$), 2.38 (s, 3 H, CH$_3$).

Indomethacin 4-methoxyphenyl ester (compound 21) was obtained upon chromatography on silica gel (EtOAc:hexanes; 20:80) as a yellow oil that solidified upon freezing (355 mg, 88%). mp=136–138° C.; $^1$H NMR (CDCl$_3$) δ 7.65–7.69 (d, 2H, J=8.5 Hz, ArH), 7.46–7.48.(d, 2H, J=8.5 Hz, ArH), 7.04–7.05 (d, 1H, J=2.4 Hz, ArH), 6.84–6.98 (m, 5H, ArH), 6.67–6.71 (dd, 1H, J=9.0 Hz and 2.5 Hz, ArH), 3.88 (s, 2H, CH$_2$), 3.83 (s, 3H, CH$_3$), 3.78 (s, 3H, CH$_3$), 2.44 (s, 3H, CH$_3$).

Indomethacin 4-acetamidophenyl ester (compound 22) was obtained upon chromatography on silica gel (EtOAc:hexanes; 20:80 then 70:30) as a yellow solid (345 mg, 83%). mp=191–193° C.; $^1$H NMR (CDCl$_3$) δ 7.66–7.69 (dd, 2H, J=8.5 Hz and 1.8 Hz, ArH), 7.46–7.49 (m, 4H, ArH), 7.16 (bs, 1H, NH), 6.99–7.04 (m, 3H, ArH), 6.87–6.89 (d, 1H, J=9.0 Hz, ArH), 6.67–6.71 (dd, 1H, J=8.9 Hz and 2.5 Hz, ArH), 3.88 (s, 2H, CH$_2$), 3.83 (s, 3H, CH$_3$), 2.44 (s, 3H, CH$_3$), 2.04 (s, 3H, CH$_3$).

Indomethacin 4-fluorophenyl ester (compound 23) was obtained upon chromatography on silica gel (EtOAc:hexanes; 10:90) as off-white solid (359 mg, 95%). mp=143–144° C.; $^1$H NMR (CDCl$_3$) δ 7.66–7.69 (dd, 2H, J=8.5 Hz and 1.8 Hz, ArH), 7.46–7.49 (dd, 2H, J=8.5 Hz and 1.9 Hz, ArH), 7.01–7.04 (m, 5H, ArH), 6.86–6.89 (d, 1H, J=9.0 Hz, ArH), 6.67–6.71 (dd, 1H, J=9.0 Hz and 2.5 Hz, ArH), 3.89 (s, 2H, CH$_2$), 3.83 (s, 3H, CH$_3$), 2.45 (s, 3H, CH$_3$).

Indomethacin 3-pyridyl ester (compound 24) was obtained upon chromatography on silica gel (EtOAc:hexanes; 20:80) as a yellow oil that solidified upon freezing (191 mg, 67%). mp=134–136° C.; $^1$H NMR (CDCl$_3$) δ 8.46–8.47 (d, 1H, J=4.6 Hz, pyridyl-H), 8.39–8.40 (d, 1H, J=2.5 Hz, pyridyl-H), 7.66–7.68 (d, 2H, J=8.4 Hz, ArH), 7.43–7.48 (d and m 3H, 2 ArH, J=8.5 Hz and 1 pyridyl-H), 7.28–7.32 (m, 1H, pyridyl-H), 7.02–7.03 (d, 1H, J=2.4 Hz, ArH), 6.85–6.88 (d, 1H, J=9.0 Hz, ArH), 6.67–6.70 (dd, 1H, J=9.0 Hz and 2.5 Hz, ArH), 3.93 (s, 2H, CH$_2$), 3.83 (s, 3H, CH$_3$), 2.46 (s, 3H, CH$_3$).

Indomethacin β-naphthyl ester (compound 25) was obtained upon chromatography on silica gel (EtOAc:hexanes; 20:80) as a crystalline yellow solid (166 mg, 41%). mp=70–72° C.; $^1$H NMR (CDCl$_3$) δ 7.82–7.85 (d, 2H, J=8.9 Hz, ArH), 7.76–7.79 (m, 1H, ArH), 7.68–7.71 (d, 2H, J=8.2 Hz, ArH), 7.54–7.55 (d, 1H, J=1.8 Hz, ArH), 7.46–7.50 (m, 4H, ArH), 7.17–7.21 (dd, 1 H, J=8.9 Hz and 2.1 Hz, ArH), 7.10–7.11 (d, 1H, J=2.3 Hz, ArH), 6.90–6.93 (d, 1H, J=9.1 Hz, ArH), 6.69–6.73 (dd, 1H, J=8.9 Hz and 2.2 Hz, ArH), 3.97 (s, 2H, CH$_2$), 3.85 (s, 3H, CH$_3$), 2.49 (s, 3H, CH$_3$).

Indomethacin N-4-ethylmorpholino ester (compound 26) was obtained upon chromatography on silica gel (EtOAc:hexanes; 40:60) as a yellow oil which solidified upon freezing (348 mg, 86%). mp=83–84° C.; $^1$H NMR (CDCl$_3$) δ 7.63–7.66 (d, 2H, J=8.4 Hz, ArH), 7.44–7.47 (d, 2H, J=8.4 Hz, ArH), 6.94–6.95 (d, 1H, J=2.4 Hz, ArH), 6.81–6.84 (d, 1H, J=9.0 Hz, ArH), 6.63–6.66 (dd, 1H, J=9.0 Hz and 2.4 Hz, ArH), 4.20–4.24 (t, 2H, J=5.8 Hz, CH$_2$), 3.82 (s, 3H, CH$_3$), 3.66 (s, 2H, CH$_2$), 3.58–3.61 (t, 4H, J=4.8 Hz, 2 CH$_2$), 2.55–2.59 (t, 2H, J=5.7 Hz, CH$_2$), 2.38–2.40 (s merged with a t, 7H CH$_3$ and 2 CH$_2$).

Indomethacin 3-phenylpropyl ester (compound 27) was obtained upon chromatography on silica gel (EtOAc:hexanes; 20:80) as a yellow oil that solidified upon freezing (393 mg, 95%). mp=81–83° C.; $^1$H NMR (CDCl$_3$) δ 7.61–7.64 (dd, 2H, J=8.4 Hz and 1.6 Hz, ArH), 7.41–7.44 (dd, 2H, J=8.5 Hz and 1.9 Hz, ArH), 7.16–7.24 (m, 2H, ArH), 7.03–7.06 (d, 2H, J=8.0 Hz, ArH), 6.97–6.98 (d, 1H, J=2.4 Hz, ArH), 6.83–6.86 (d, 1H, J=9.0 Hz, ArH), 6.64–6.68 (dd, 1 H J=9.0 Hz and 2.5 Hz, ArH), 4.08–4.12 (t, 2H, J=6.4 Hz, CH$_2$), 3.81 (s, 3H, CH$_3$), 3.65 (s, 2H, CH$_2$), 2.55–2.60 (t, 2H, J=8.1 Hz, CH$_2$), 2.39 (s, 3H, CH$_3$), 1.87–1.96 (m, 2H, CH$_2$).

Indomethacin a-naphthyl ester (compound 28) was obtained upon chromatography on silica gel (EtOAc:hexanes; 30:70) as a crystalline white solid (378 mg, 93%). $^1$H NMR (CDCl$_3$) δ 7.82–7.85 (d, 1H, J=8.9 Hz, ArH), 7.61–7.71 (m, 3H, ArH), 7.41–7.49 (m, 6H, ArH), 7.37–7.39 (m, 1H, ArH), 7.22–7.24 (d, 1H, J=7.2 Hz, ArH), 6.91–6.94 (d, 1H, J=9.0 Hz, ArH), 6.70–6.74 (dd, 1H, J=8.9 Hz and 2.2 Hz, ArH), 4.07 (s, 2H, CH$_2$), 3.82 (s, 3H, CH$_3$), 2.51 (s, 3H, CH$_3$).

Indomethacin-(2-tert-BOC-aminoethyl)ester (compound 29) was obtained upon chromatography on silica gel (EtOAc:hexanes; 30:70 and then 60:40) as a pale yellow oil which eventually solidified upon freezing (221 mg, 53%). $^1$H NMR (CDCl$_3$) δ 7.65–7.68 (d, 2H, J=8.4 Hz, ArH), 7.46–7.49 (d, 2 H, J=8.5 Hz, ArH), 6.95–6.96 (d, 1H, J=2.4 Hz, ArH), 6.85–6.88 (d, 1H, J=9.0 Hz, ArH), 6.65–6.69 (dd, 1H, J=9.0 Hz and 2.5 Hz, ArH), 4.65 (bs, 1H, NH), 4.14–4.18 (t, 2H,J=5.4 Hz, CH$_2$), 3.84(s, 3H, CH$_3$), 3.68 (s, 2H, CH$_2$), 3.36–3.38 (m, 2H, CH$_2$), 2.39 (s, 3H, CH$_3$), 1.42 (s, 9H, CH$_3$).

The structures and IC$_{50}$ values for indomethacin and Compounds 2 through 29 are set out in Table 1 below.

TABLE 1

Selective COX-2 Inhibition by Ester Derivatives of Indomethacin

| Compound | X | IC$_{50}$ (μM)[a] | | Selectivity[b] |
|---|---|---|---|---|
| | | COX-2 | COX-1 | |
| NS-398 | H-N(SO$_2$CH$_3$)-C$_6$H$_3$(O-cyclohexyl)(NO$_2$) | 0.12 | >66 | >550 |

TABLE 1-continued

Selective COX-2 Inhibition by Ester Derivatives of Indomethacin

| Compound | X | IC$_{50}$ ($\mu$M)[a] COX-2 | COX-1 | Selectivity[b] |
|---|---|---|---|---|
| 2-methyl-4-phenyl-5-sulfonamidophenyl oxazolo | | 0.06 | >66 | >1100 |
| 1: Indomethacin | H | 0.75 | 0.05 | 0.066 |
| 2 | CH$_3$ | 0.25 | 33 | 132 |
| 3 | ethyl | 0.10 | >66 | 660 |
| 4 | n-propyl | 0.10 | >66 | 660 |
| 5 | isopropyl | 0.25 | 37 | 148 |
| 6 | n-butyl | 0.05 | >66[c] | >1320 |
| 7 | n-pentyl | 0.05 | >66[c] | >1320 |
| 8 | n-hexyl | 0.062 | >66[c] | >1064 |
| 9 | cyclohexyl | 0.125 | >66[c] | >528 |

TABLE 1-continued

Selective COX-2 Inhibition by Ester Derivatives of Indomethacin

| Compound | X | IC$_{50}$ ($\mu$M)[a] COX-2 | COX-1 | Selectivity[b] |
|---|---|---|---|---|
| 10 | cyclohexylmethyl | 1.00 | >66 | >66 |
| 11 | n-octyl | 0.04 | >66[c] | >1650 |
| 12 | -CH$_2$CH$_2$OCH$_2$CH$_2$CH$_2$CH$_3$ | 0.06 | >66[c] | >1100 |
| 13 | heptenyl | 0.05 | >66[c] | >1320 |
| 14 | heptynyl | 0.25 | >66 | >264 |
| 15 | methyl-hexynyl | 0.12 | >66 | >550 |
| 16 | n-nonyl | 0.09 | >66 | >733 |
| 17 | phenyl | 0.40 | >66 | 165 |
| 18 | 3,5-dimethylphenyl | >8.0 | >66 | — |

TABLE 1-continued

Selective COX-2 Inhibition by Ester Derivatives of Indomethacin

| Compound | X | IC$_{50}$ ($\mu$M)[a] | | Selectivity[b] |
|---|---|---|---|---|
| | | COX-2 | COX-1 | |
| 19 | 4-(SCH$_3$)phenyl | 0.30 | 2.60 | 8.66 |
| 20 | 2-(SCH$_3$)phenyl | 0.062 | >66[c] | >1064 |
| 21 | 4-(OCH$_3$)phenyl | 0.040 | >66 | >1650 |
| 22 | 4-(NHC(O)CH$_3$)phenyl | 0.055 | 66 | 1200 |
| 23 | 4-fluorophenyl | 0.075 | 3.0 | 40 |
| 24 | 3-pyridyl | 0.05 | 2.5 | 50 |
| 25 | 2-naphthyl | >8.0 | >66 | — |

TABLE 1-continued

Selective COX-2 Inhibition by Ester Derivatives of Indomethacin

| Compound | X | IC$_{50}$ ($\mu$M)[a] COX-2 | COX-1 | Selectivity[b] |
|---|---|---|---|---|
| 26 | (3-morpholinopropyl) | 0.68 | >66[c] | >97 |
| 27 | (3-phenylpropyl) | 0.040 | >66[c] | >1650 |
| 28 | (1-naphthyl) | 5.0 | >66 | >13 |
| 29 | (3-(Boc-amino)propyl) | 0.045 | >66[c] | >1466 |

[a]IC$_{50}$ values were determined by incubating several inhibitor concentrations in DMSO with human COX-2 (66 nM) or ovine COX-1 (44 nM) for 20 min at rt followed by initiation of the cyclooxygenase reaction with the addition of $^{14}$C-AA (50 $\mu$M) at 37° C. for 30 sec. Isolation and quantification of prostanoid products was conducted as described before. Assays were run in duplicate.
[b]Ratio of IC$_{50}$ (COX-1):IC$_{50}$ (COX-2).
[c]>90% activity remains at these inhibitor concentrations.

Discussion of Derivatives with Aliphatic Ester Moiety

Conversion of the free carboxylic acid group in indomethacin to the methyl ester afforded compound 2 which displayed selective COX-2 inhibition. Compound 2 was 132 times selective as a COX-2 inhibitor [compound 2: IC$_{50}$ (COX-2)~0.25 $\mu$M; IC$_{50}$ (COX-1)~33 $\mu$M]. Thus, esterification of the carboxylic acid in indomethacin increased the inhibitory potency against COX-2, but had a detrimental effect on the potency for COX-1 inhibition. Chain length extension studies of the methyl group in compound 2 to higher alkyl homologs revealed significant increases in potency and selectivity against COX-2. For example, the heptyl ester (compound 11) displayed increased potency (IC$_{50}$ (COX-2)~40 nM) and increased selectivity (>1650) for COX-2 compared to the methyl ester (compound 2). Incorporation of oxygen atom in the 3 position (compound 12) or a trans-double bond in the 2,3 position (compound 13) also led to increased potency and selectivity for COX-2. The cyclohexylethyl ester (compound 10) and the hept-2-ynyl analog (compound 14), however, were less effective as COX-2 inhibitors [compound 10: IC$_{50}$ (COX-2)~1.00 $\mu$M; IC$_{50}$ (COX-1)>66 $\mu$M; compound 14: IC$_{50}$ (COX-2)~0.25 $\mu$M; IC$_{50}$ (COX-1) >66 $\mu$M].

Discussion of Derivatives with Aromatic Ester Moiety

Transformation of the carboxylic acid moiety in indomethacin to a phenyl ester (compound 17) also led to a selective COX-2 inhibitor [IC$_{50}$ (COX-2)~0.40 $\mu$M; IC$_{50}$ (COX-1)>66 $\mu$M] (Table 1). Introduction of methylene spacers between the phenyl ring and the ester oxygen generated the 3-phenylpropyl ester (compound 27) which was a much more potent and selective COX-2 inhibitor than compound 17 [IC$_{50}$ (COX-2)~0.040 $\mu$M; IC$_{50}$ (COX-1)>66 $\mu$M], whereas the bulkier 3,5-dimethylphenyl- ester (compound 18) and β-naphthyl-ester (compound 25) were less active against COX-2 [$IC_{50}$ (COX-2)>8 μM; $IC_{50}$ (COX-1)>66 μM]. Interestingly, selective inhibition of COX-2 by the compounds having an aromatic ester substituent was extremely sensitive to the type and position of the various substituents on the phenyl ring. For instance, presence of a methylmercapto group in the 4-position of the phenyl group afforded compound 19, which was only ~8.5 times selective as a COX-2 inhibitor, whereas the corresponding 2-methyl)mercaptophenyl isomer (compound 20) was >1064-fold selective as a COX-2 inhibitor. Furthermore, replacement of the 4-methylmercapto group with a 4-methoxy group yielded compound 21, which displayed extremely high affinity for COX-2 and was >1650-fold selective as a COX-2 inhibitor. Like the 4-methylmercaptophenyl ester (compound 19), the 4-fluorophenyl ester (compound 23) and the 3-pyridyl ester (compound 24) were also less selective as COX-2 inhibitors.

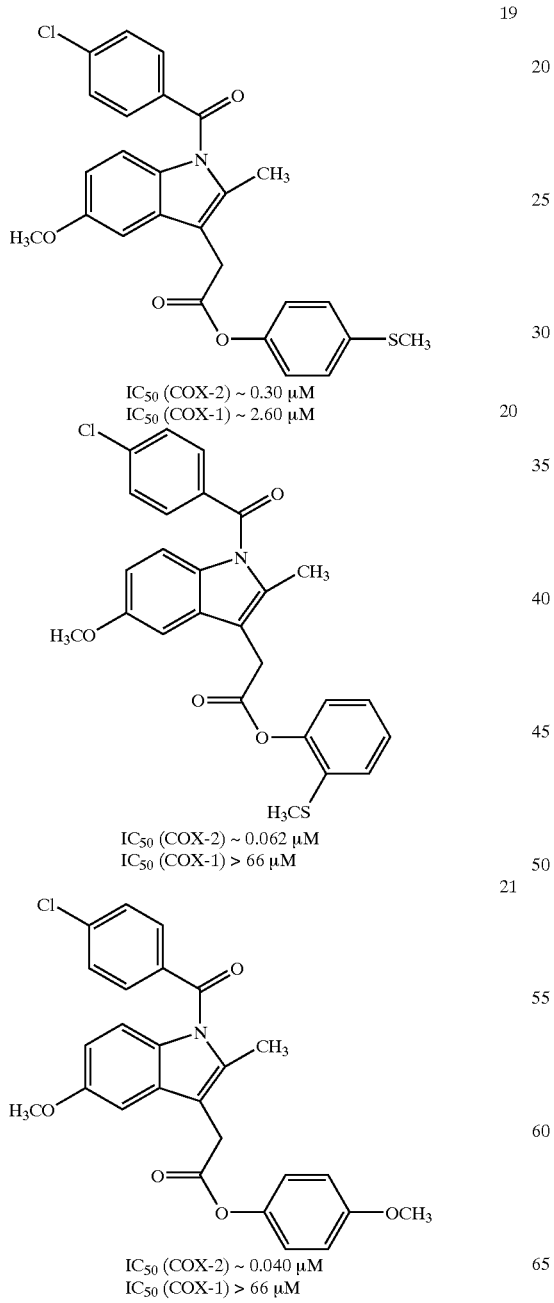

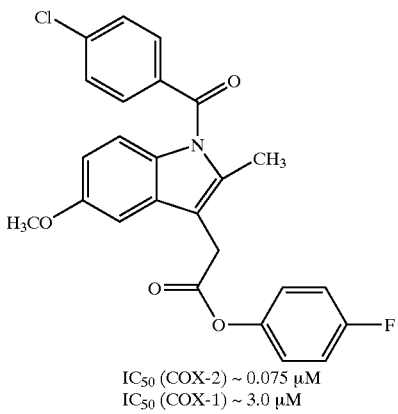

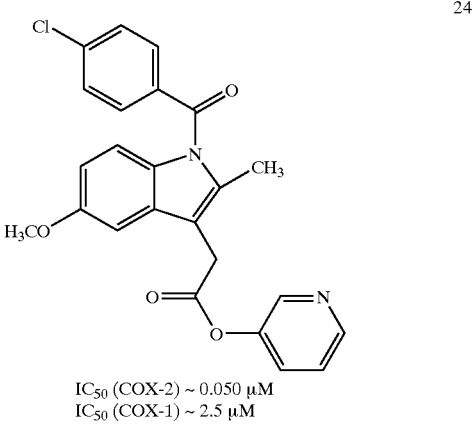

Example II

Derivatives with Amide Moiety.

The following carboxylic acid amide derivatives of indomethacin, designated as compounds 28 through 58, were made. (Note: compounds 28, 29, and 36 through 40 are also disclosed in the above-discussed U.S. Pat. Nos. 3,285,908 and 3,336,194, both to Shen, assignor to Merck & Co., Inc.)

Indomethacin-N-methyl amide (compound 28) was obtained upon chromatography on silica gel (EtOAc:hexanes; 10:90 then 50:50) as a bright yellow solid (271 mg, 79%). mp=187–189° C.; $^1$H NMR (CDCl$_3$) δ 7.64–7.67 (dd, 2H, J=6.6 Hz and 1.9 Hz, ArH), 7.47–7.50 (dd, 2H, J=6.7 Hz and 1.9 Hz, ArH), 6.88–6.89 (dd, 1H, J=9.1 Hz and 2.5 Hz, ArH), 6.84–6.87 (d, 1H, J=9.0 Hz, ArH), 6.68–6.72 (dd, 1H, J=9.1 Hz and 2.5 Hz, ArH), 5.22 (bs, 1 H, NH), 3.83 (s, 3H, CH$_3$), 3.65 (s, 2H, CH$_2$), 2.75–2.76 (d, 3H, J=4.8 Hz, CH$_3$), 2.39 (s, 3H, CH$_3$).

Indomethacin-N-ethan-2-ol amide (compound 29) was obtained upon chromatography on silica gel (EtOAc) as a pale yellow solid (143 mg, 39%). mp=162–164° C.; $^1$H NMR (CDCl$_3$) δ 7.66–7.68 (dd, 2H, J=6.7 Hz and 1.7 Hz, ArH), 7.47–7.50 (dd, 2H, J=6.9 Hz and 1.9 Hz, ArH), 6.85–6.89 (d and s, 2H, J=9.2 Hz, ArH), 6.68–6.72 (dd, 1H, J=9.0 Hz and 2.5 Hz, ArH), 6.03 (bs, 1H, NH), 3.82 (s, 3H, CH$_3$), 3.67 (bs, 4H, 2CH$_2$), 3.35–3.40 (q, 2H, J=4.8 Hz, CH$_2$), 2.44 (bs, 1H, OH), 2.39 (s, 3H, CH$_3$).

Indomethacin-N-octyl amide (compound 30) was obtained upon chromatography on silica gel (EtOAc:hexanes; 30:70) as a yellow solid (164 mg, 42%). mp=109–111° C.; $^1$H NMR (CDCl$_3$) δ 7.62–7.65 (d, 2H, J=8.2 Hz, ArH), 7.46–7.49 (d, 2H, J=8.2 Hz, ArH), 6.85–6.89 (m, 2H, ArH), 6.68–6.71 (d, 1H, J=8.9 Hz, ArH), 5.67 (s, 1H, NH), 3.82 (s, 3H, CH$_3$), 3.64 (s, 2H, CH$_2$), 3.16–3.22 (m, 2H, CH$_2$), 2.38 (s, 3H, CH$_3$), 1.39 (m, 2H, CH$_2$), 1.19 (m, 10H, 5CH$_2$), 0.83–0.88 (t, J=6.2 Hz, CH$_3$).

Indomethacin-N-nonyl amide (compound 31) was obtained upon chromatography on silica gel (EtOAc:hexanes; 30:70) as a yellow solid (191 mg, 47%). mp=128–130° C.; $^1$H NMR (CDCl$_3$) δ 7.64–7.67 (d, 2H, J=8.4 Hz, ArH), 7.47–7.50 (d, 2H, J=8.4 Hz, ArH), 6.89 (s, 1H, ArH), 6.85–6.88 (d, J=8.9 Hz, ArH), 6.68–6.72 (dd, 1H, J=9.0 Hz and 2.4 Hz, ArH), 5.60–5.63 (bt, J=5.3 Hz, NH), 3.82 (s, 3H, CH$_3$), 3.64 (s, 2H, CH$_2$), 3.16–3.22 (m, 2H, CH$_2$), 2.38 (s, 3H, CH$_3$), 1.36–1.41 (m, 2H, CH$_2$), 1.19–1.28 (m, 12H, 6CH$_2$), 0.84–0.89 (t, J=6.5 Hz, CH$_3$).

Indomethacin-N-(2-methylbenzyl) amide (compound 32) was obtained upon chromatography on silica gel (EtOAc:hexanes; 50:50) as a yellow solid (218 mg, 56%). mp=177–179° C.; $^1$H NMR (CDCl$_3$) δ 7.60–7.61 (d, 2H, J=8.1 Hz, ArH), 7.44–7.46 (d, 2H, J=8.1 Hz, ArH), 7.06–7.15 (m, 4H, ArH), 6.83–6.89 (m, 2H, ArH), 6.67–6.70 (d, 1H, J=8.1 Hz, ArH), 5.84 (s, 1H, NH), 4.40–4.41 (d, 2H, J=5.3 Hz, CH$_2$), 3.79 (s, 3H, CH$_3$), 3.70 (s, 2H, CH$_2$), 2.37 (s, 3H, CH$_3$), 2.19 (s, 3H, CH$_3$).

Indomethacin-N-(4-methylbenzyl) amide (compound 33) was obtained upon recrystallization from methanol as a yellow solid (142 mg, 37%). mp=191–192° C.; $^1$H NMR (CDCl$_3$) δ 7.63–7.60 (d, 2H, J=8.5 Hz, ArH), 7.46–7.44 (d, 2H, J=8.4 Hz, ArH), 7.08–7.01 (m, 4H, ArH), 6.88 (s, 1H, ArH), 6.87–6.85 (d, 1H, J=6.3 Hz, ArH), 6.71–6.67 (dd, 1H, J=9.0 Hz and 2.4 Hz, ArH), 5.89 (bt, 1H, NH), 4.38–4.36 (d, 2H, J=5.9 Hz, CH$_2$), 3.78 (s, 3H, CH$_3$), 3.69 (s, 2H, CH$_2$), 2.35 (s, 3H, CH$_3$), 2.30 (s, 3H, CH$_3$).

Indomethacin-N-((R)-4-dimethylbenzyl) amide (compound 34) was obtained upon recrystallization from methanol to yield a pale yellow solid (124 mg, 31%). mp=201–202° C.; $^1$H NMR (CDCl$_3$) δ 7.62–7.64 (d, 2H, J=8.4 Hz, ArH), 7.45–7.48 (d, 2H, J=8.6 Hz, ArH), 7.01–7.08 (m, 4H, ArH), 6.87–6.90 (d, 1H, J=9.0 Hz, ArH), 6.83–6.84 (d, 1H, J=2.3 Hz, ArH), 6.68–6.72 (dd, 1H, J=9.0 Hz and 2.4 Hz, ArH), 5.76–5.78 (bd, 1H, J=8.0 Hz, NH), 5.09–5.14 (m, 1H, CH), 3.76 (s, 3H, CH$_3$), 3.63–3.64 (d, 2H, J=2.8 Hz, CH$_2$), 2.34 (s, 3H, CH$_3$), 2.30 (s, 3H, CH$_3$), 1.35–1.38 (d, 3H, J=6.8 Hz, CH$_3$).

Indomethacin-N-((S)-4-dimethylbenzyl) amide (compound 35) was obtained upon recrystallization from methanol as a pale yellow solid (163 mg, 41%). mp=200–201° C.; $^1$H NMR (CDCl$_3$) δ 7.53–7.55 (d, 2H, J=8.3 Hz, ArH), 7.37–7.40 (d, 2H, J=8.4 Hz, ArH), 6.94–7.01 (m, 4H, ArH), 6.76–6.82 (m, 2H, ArH), 6.61–6.64 (dd, 1H, J=9.0 Hz and 2.5 Hz, ArH) 5.77–5.79 (bd, 1H, J=7.8 Hz, NH), 5.02–5.07 (m, 1H, CH), 3.69 (s, 3H, CH$_3$), 3.58–3.59 (d, 2H, J=2.9 Hz CH$_2$), 2.27 (s, 3H, CH$_3$), 2.23 (s, 3H, CH$_3$), 1.28–1.30 (d, 3H, J=6.9 Hz, CH$_3$).

Comparison. Indomethacin-N-methylphenethyl amide (compound 36) was obtained upon chromatography on silica gel (EtOAc:hexanes; 50:50) as a yellow solid (288 mg, 72%). mp=61–63° C.; $^1$H NMR (CDCl$_3$) δ 7.64–7.67 (d, 2H, J=8.4 Hz, ArH), 7.45–7.48 (d, 2H, J=8.5 Hz, ArH), 7.02 (d, 1H, J=2.4 Hz, ArH), 6.81–6.84 (d, 1H, J=9.0 Hz, ArH), 6.63–6.66 (dd, 1H, J=9.0 Hz and 2.5 Hz, ArH), 3.82 (s, 3H, CH$_3$), 3.71 (s, 2H, CH$_2$), 3.57–3.60 (t, 2H, J=5.4 Hz, CH$_2$), 3.43–3.46 (t, 2H, J=5.3 Hz, CH$_2$), 2.38 (s, 3H, CH$_3$), 1.59–1.61 (m, 2H, CH$_2$), 1.52–1.53 (m, 2H, CH$_2$), 1.42–1.43 (m, 2H, CH$_2$).

Comparison. Indomethacin-N-piperidinyl amide (compound 37) was obtained upon chromatography on silica gel (EtOAc:hexanes; 40:60) as a pale yellow solid (146 mg, 41%). mp=161–163° C.; $^1$H NMR (CDCl$_3$) δ 7.64–7.67 (d, 2H, J=8.4 Hz, ArH), 7.45–7.48 (d, 2H, J=8.5 Hz, ArH), 7.02 (d, 1H, J=2.4 Hz, ArH), 6.81–6.84 (d, 1H, J=9.0 Hz, ArH), 6.63–6.66 (dd, 1H, J=9.0 Hz and 2.5 Hz, ArH), 3.82 (s, 3H, CH$_3$), 3.71 (s, 2H, CH$_2$), 3.57–3.60 (t, 2H, J=5.4 Hz, CH$_2$), 3.43–3.46 (t, 2H, J=5.3 Hz, CH$_2$), 2.38 (s, 3H, CH$_3$), 1.59–1.61 (m, 2H CH$_2$), 1.52–1.53 (m, 2H, CH$_2$), 1.42–1.43 (m, 2H, CH$_2$).

Indomethacin-N-(2-phenethyl) amide (compound 38) was obtained upon chromatography on silica gel (EtOAc:hexanes; 30:70) as a bright yellow solid (169 mg, 44%). mp=148–150° C.; $^1$H NMR (CDCl$_3$) δ 7.58–7.60 (d, J=8.4 Hz, ArH), 7.46–7.48 (d, 2H, J=8.5 Hz, ArH), 7.12–7.14 (m, 3H, ArH), 6.85–6.95 (m, 4H, ArH), 6.69–6.73 (dd, 1H, J=8.9 Hz and 2.4 Hz, ArH), 5.61 (s, 1H, NH), 3.81 (s3H, CH$_3$), 3.59 (s, 2H, CH$_2$), 3.43–3.49 (m, 2H, CH$_2$), 2.68–2.72 (t, 2H, J=6.7 Hz, CH$_2$), 2.04 (s, 3H, CH$_3$).

Indomethacin-N-(4-fluorophenyl) amide (compound 39) was obtained upon chromatography on silica gel (EtOAc:hexanes; 5:95 to 20:80) as an orange solid (217 mg, 57%). mp=200–202° C.; $^1$H NMR (CDCl$_3$) δ 7.65–7.67 (d, 2H, J=8.3 Hz, ArH), 7.47–7.50 (d, 2H, J=8.3 Hz, ArH), 7.32–7.35 (m, 3H, ArH), 6.94–6.99 (m, 3H, ArH, NH), 6.85–6.88 (d, 1H, J=9.0 Hz, ArH), 6.70–6.73 (dd, 1H, J=9.0 Hz and 2.0 Hz, ArH), 3.81 (s, 3H, CH3), 3.79 (s, 2H, CH$_2$), 2.45 (s, 3H, CH$_3$).

Indomethacin-N-(4-chlorophenyl) amide (compound 40) was obtained upon recrystallization from methanol as a pale yellow solid (234 mg, 56%). mp=209–210° C.; $^1$H NMR (CDCl$_3$) δ 7.58–7.61 (d, 2H, J=8.2 Hz, ArH), 7.40–7.42 (d, 2H, J=8.2 Hz, ArH), 7.13–7.27 (m, 5H, ArH), 6.84 (s, 1H, NH), 6.77–6.80 (d, 1H, J=9.0 Hz, ArH), 6.62–6.65 (d, 1H, J=9.0 Hz, ArH), 3.72 (s, 2H, CH$_2$), 3.72 (s, 3H, CH$_3$), 2.37 (s, 3H, CH$_3$).

Indomethacin-N-(4-acetamidophenyl) amide (compound 41) was obtained upon recrystallization from methanol as a pale yellow solid (221 mg, 54%). mp=256–257° C.; $^1$H NMR (DMSO-d$_6$) δ 10.14 (s, 1H, NH), 9.86 (s, 1H, NH), 7.62–7.70 (m, 4H, ArH), 7.48 (s, 4H, ArH), 7.18 (d, 1H, J=2.3 Hz, ArH), 6.90–6.93 (d, 1H, J=9.0 Hz, ArH), 6.68–6.72 (dd, 1H, J=9.1 Hz and 2.5 Hz, ArH), 3.73 (s, 3H, CH$_3$), 3.71 (s, 2H, CH$_2$), 2.27 (s, 3H, CH$_3$), 1.99 (s, 3H, CH$_3$).

Indomethacin-N-(4-methylmercapto)phenyl amide (compound 42) was obtained upon chromatography on silica gel (EtOAc:hexanes; 50:50) as a bright yellow solid (162 mg, 40%). mp=195–196° C.; $^1$H NMR (CDCl$_3$) δ 7.67–7.70 (d, 2H, J=8.4 Hz, ArH), 7.48–7.50 (d, 2H, J=8.4 Hz, ArH), 7.30–7.33 (d, 2H, J=8.6 Hz, ArH), 7.17–7.22 (m, 3H, 2 ArH and NH), 6.92–6.93 (d, 1H, J=2.3 Hz, ArH), 6.85–6.88 (d, 1H, J=9.0 Hz, ArH), 6.69–6.73 (dd, 1H, J=9.0 Hz and 2.4 Hz, ArH), 3.80 (s, 3H, CH$_3$), 3.79 (s, 2H, CH$_2$), 2.45 (s, 3H, C$_3$), 2.44 (s, 3H, CH$_3$).

Indomethacin-N-(3-methylmercaptophenyl) amide (compound 43) was obtained upon chromatography on silica gel (EtOAc:hexanes; 15:85) as a yellow solid (218 mg, 54%). mp=129–131° C.; $^1$H NMR (CDCl$_3$) δ 7.62–7.64 (d, 2H, J=8.2 Hz, ArH), 7.45–7.48 (d, 2H, J=8.4 Hz, ArH), 7.39 (s, 1H, NH), 7.09–7.18 (m, 2H, ArH), 6.94–6.96 (m, 3H, ArH), 6.86–6.89 (d, 1H, J=9.0 Hz), 6.69–6.72 (d, 1H, J=8.9 Hz, ArH), 3.80 (s, 3H, CH$_3$), 3.78 (s, 2H, CH$_2$), 2.42 (s, 3H, CH$_3$).

Indomethacin-N-(4-methoxyphenyl) amide (compound 44) was obtained upon chromatography on silica gel (EtOAc:hexanes; 10:90 to 25:75) as an orange solid (239 mg, 61%). mp=201–202° C.; $^1$H NMR (CDCl$_3$) δ 7.67–7.70 (dd, 2H, J=6.8 Hz and 1.8 Hz, ArH), 7.48–7.51 (d, 2H, J=7.1 Hz, ArH), 7.28–7.29 (d, 1H, J=2.0 Hz, ArH), 7.20 (s, 1H, NH), 6.94–6.95 (d, 1H, J=2.4 Hz, ArH), 6.86–6.89 (d, 1H, J=9.0 Hz, ArH), 6.78–6.84 (m, 2H, ArH), 6.69–6.73 (dd, 1H, J=9.0 Hz and 2.4 Hz, ArH), 3.81 (s, 3H, CH$_3$), 3.79 (s, 2H, CH$_2$), 3.76 (s, 3H, CH$_3$), 2.45 (s, 3H, CH$_3$).

Indomethacin-N-(3-ethoxyphenyl) amide (compound 45) was obtained upon recrystallization from methanol as a bright yellow solid (297 mg, 74%). mp=152–154° C.; $^1$H NMR (CDCl$_3$) δ 7.68–7.70 (d, 2H, J=8.4 Hz, ArH), 7.48–7.51 (d, 2H, J=8.4 Hz, ArH), 7.24 (s, 1H, NH), 7.13–7.18 (m, 2H, ArH), 6.94–6.82 (m, 3H, ArH), 6.70–6.73 (dd, 1H, J=9.0 Hz and 2.4 Hz), 6.61–6.65 (dd, 1H, J=8.2 Hz and 1.7 Hz, ArH), 3.96–4.03 (q, 2H, J=7.0 Hz, CH$_2$), 3.81 (s, 3H, CH$_3$), 3.80 (s, 2H, CH$_2$), 2.45 (s, 3H, CH$_3$), 1.36–1.40 (t, 3H, J=7.0 Hz, CH$_3$).

Indomethacin-N-(3,4,5-trimethoxyphenyl) amide (compound 46) was obtained upon chromatography on silica gel (EtOAc:hexanes; 10:90 to 30:70) as a light orange solid (191 mg, 44%). mp=239–241° C.; $^1$H NMR (CDCl$_3$) δ 7.67–7.69 (d, 2H, J=8.5 Hz, ArH), 7.48–7.51 (d, 2H, J=8.5 Hz, ArH), 7.20 (s, 1H, NH), 6.94 (d, 1H, J=8.9 Hz, ArH), 6.70–6.74 (m, 3H, ArH), 3.78–3.81 (m, 14H, 3CH$_3$ & CH$_2$), 2.45 (s, 3H, CH$_3$).

Indomethacin-N-(3-pyridyl) amide (compound 47) was obtained upon chromatography on silica gel (EtOAc:hexanes; 50:50 to 75:25) as a yellow solid (190 mg, 52%). mp=204–205° C.; $^1$H NMR (CDCl$_3$) δ 8.39–8.40 (d, 1H, J=2.1 Hz, ArH), 8.32–8.34 (d, 1H, J=4.4 Hz, ArH), 8.04–8.08 (m, 1H, ArH), 7.66–7.70 (m, 2H, ArH), 7.48–7.52 (m, 2H, ArH), 7.38 (s, 1H, NH), 7.22–7.25 (m, 1H, ArH), 6.93–6.94 (d, 1H, J=2.4Hz, ArH), 6.85–6.88 (d, 1H, J=9.1 Hz, ArH), 6.70–6.74 (dd, 1H, J=9.1 Hz and 2.5 Hz, ArH), 3.84 (s, 2H, CH$_2$), 3.81 (s, 3H, CH$_3$), 2.47 (s, 3H, CH$_3$).

Indomethacin-N-5-((2-chloro)pyridyl) amide (compound 48) was obtained upon chromatography on silica gel (EtOAc:hexanes; 5:95 to 50:50) as a pale yellow solid (221 mg, 56%). mp=196–198 C; $^1$H NMR (CDCl$_3$) δ 8.19–8.20 (d, 1H, J=2.8 Hz, ArH), 8.03–8.06 (dd, 1H, J=8.7 Hz and 2.9 Hz, ArH), 7.59–7.63 (m, 2H, ArH), 7.46–7.51 (m, 3H, ArH), 7.24 (s, 1H, NH), 6.92–6.93 (d, 1H, J=2.4 Hz, ArH), 6.84–6.87 (d, 1H, J=9.0 Hz, ArH), 6.70–6.74 (dd, 1H, J=9.1 Hz and 2.5 Hz, ArH), 3.84 (s, 2H, CH$_2$), 3.82 (s, 3H, CH$_3$), 2.46 (s, 3H, CH$_3$).

Indomethacin-N-5-((1-ethyl)pyrazolo) amide (compound 49) was obtained upon recrystallization from methanol as a pale yellow solid (153 mg, 40%). mp=193–194° C.; $^1$H NMR (CDCl$_3$) δ 7.99 (bs, 1H, NH), 7.66–7.68 (d, 2H, J=8.2 Hz, ArH), 7.47–7.50 (m, 3H, ArH), 7.00 (s, 1H, ArH), 6.83–6.86 (d, 1H, J=9.0 Hz, ArH), 6.69–6.72 (d, 1H, J=8.9 Hz, ArH), 6.35 (s, 1H, ArH), 4.01–4.04 (bd, 2H, J=6.8 Hz, CH$_2$), 3.90 (s, 2H, CH$_2$), 3.82 (s, 3H, CH$_3$), 2.47 (s, 3H, CH$_3$), 1.24–1.29 (t, 3H, J=7.1 Hz, CH$_3$).

Indomethacin-N-(3-chloropropyl) amide (compound 50) was obtained upon chromatography on silica gel (EtOAc:hexanes; 30:70) as a off-white solid (153 mg, 40%). 1H NMR (DMSO-d$_6$) δ 8.11 (bs, 1H, NH), 7.62–7.69 (m, 4H, ArH), 7.09 (s, 1H, ArH), 6.92–6.95 (d, 1H, J=8.9 Hz, ArH), 6.68–6.71 (d, 1H, J=8.8 Hz, ArH), 3.80 (s, 3H, CH$_3$), 3.58–3.67 (t, 2H, J=6.3 Hz, CH$_2$), 3.52 (s, 2H, CH$_2$), 3.15–3.17 (m, 2H, CH$_2$), 2.20 (s, 3H, CH$_3$), 1.81–1.85 (t, 2H, J=6.5 Hz, CH$_2$).

Indomethacin-N-methoxycarbonylmethyl amide (compound 51) was obtained upon chromatography on silica gel (EtOAc:hexanes; 30:70) as a yellow solid (265 mg, 76%). $^1$H NMR (CDCl$_3$) δ 7.66–7.68 (dd, 2H, J=6.7 Hz and 1.7 Hz, ArH), 7.47–7.50 (dd, 2H, J=6.9 Hz and 1.9 Hz, ArH), 6.92–6.95 (m, 2H, ArH), 6.70–6.73 (m, 1H, ArH), 6.03 (bs, 1H, NH), 3.98–4.00 (d, 2H, J=5.5 Hz, CH$_2$), 3.84 (s, 3H, CH$_3$), 3.71 (s, 3H, CH$_3$), 3.69 (s, 2H, CH$_2$), 2.38 (s, 3H, CH$_3$).

Indomethacin-N-2-(2-L-methoxycarbonylethyl) amide (compound 52) was obtained upon chromatography on silica gel (EtOAc:hexanes; 30:70 and then 50:50) as a yellow solid (300 mg, 84%). $^1$H NMR (CDCl$_3$) δ 7.67–7.70 (dd, 2H, J=8.5 Hz and 1.85 Hz, ArH), 7.47–7.50 (dd, 2H, J=8.4 Hz and 1.9 Hz, ArH), 6.91–6.96 (m, 2H, ArH), 6.69–6.73 (m, 1H, ArH), 6.16–6.18 (d, 1H, J=7.4 Hz, NH), 4.57–4.62 (m, 1H, CH), 3.83 (s, 3H, CH$_3$), 3.70 (s, 3H, CH$_3$), 3.65 (s, 2H, CH$_2$), 2.37 (s, 3H, CH$_3$), 1.32–1.34 (d, 3H, J=7.2 Hz, CH$_3$).

Indomethacin-N-2-(2-D-methoxycarbonylethyl) amide (compound 53) was obtained upon chromatography on silica gel (EtOAc:hexanes; 40:60) as a yellow solid (803 mg, 67%). $^1$H NMR (CDCl$_3$) δ 7.67–7.70 (dd, 2H, J=8.5 Hz and 1.85 Hz, ArH), 7.47–7.50 (dd, 2H, J=8.4 Hz and 1.9 Hz, ArH), 6.91–6.96 (m, 2H, ArH), 6.69–6.73 (dd, 1H, ArH), 6.16–6.18 (d, 1H, J=7.4 Hz, NH), 4.57–4.62 (m, 1H, CH), 3.83 (s, 3H, CH$_3$), 3.70 (s, 3H, CH$_3$), 3.65 (s, 2H, CH$_2$), 2.36 (s, 3H, CH$_3$), 1.32–1.34 (d, 3H, J=7.2 Hz, CH$_3$).

Indomethacin-N-(4-methoxycarbonylbenzyl) amide (compound 54) was obtained upon chromatography on silica gel (EtOAc:hexanes; 40:60) as a yellow solid (198 mg, 47%). $^1$H NMR (CDCl$_3$) δ 7.91–7.94 (d, 2H, J=6.8 Hz, ArH), 7.61–7.65 (d, 2H, J=8.7 Hz, ArH), 7.45–7.48 (d, 2H, J=9.0 Hz, ArH), 7.19–7.21 (d, 2H, J=8.3 Hz, ArH), 6.83–6.88 (m, 2H, ArH), 6.68–6.72 (dd, 1H, J=9.0 Hz and 2.4 Hz, ArH), 5.97–5.99 (bt, 1H, J=5.9 Hz, NH), 4.454.47 (d, 2H, J=6.1 Hz, CH$_2$), 3.90 (s, 3H, CH$_3$), 3.83 (s, 3H, CH$_3$), 3.72 (s, 2H, CH$_2$), 2.38 (s, 3H, CH$_3$).

Indomethacin-N-(4-methoxycarbonylmethylphenyl) amide (compound 55) was obtained upon chromatography on silica gel (EtOAc:hexanes; 20:80) as an yellow solid (100 mg, 23%). $^1$H NMR (CDCl$_3$) δ 7.67–7.70 (d, 2H, J=8.5 Hz, ArH), 7.48–7.51 (d, 2H, J=8.5 Hz, ArH), 7.33–7.36 (d, 2H, J=8.4 Hz, ArH), 7.18–7.23 (d and bs, 3H, ArH and NH), 6.92–6.93 (d, 1H, J=2.3 Hz, ArH), 6.85–6.88 (d, 1H, J=9.0 Hz, ArH), 6.70–6.73 (dd, 1H, J=9.0 Hz and 2.0 Hz, ArH), 3.81 (s, 5H, CH$_2$ and CH$_3$), 3.67 (s, 3H, CH$_3$), 3.56 (s, 3H, CH$_2$), 2.45 (s, 3H, CH$_3$).

Indomethacin-N-(2-pyrazinyl) amide (compound 56) was obtained upon chromatography on silica gel (EtOAc:hexanes; 30:70 to 50:50) as a bright yellow solid (251 mg, 69%). $^1$H NMR (CDCl$_3$) δ 9.58 (d, 1H, J=1.4 Hz, ArH), 8.33–8.34 (d, 1H, J=2.5 Hz, ArH), 8.16–8.17 (m, 1H, ArH), 7.86 (bs, 1H, NH), 7.69–7.71 (d, 2H, J=8.5 Hz, ArH), 7.49–7.51 (d, 2H, J=8.5 Hz, ArH), 6.92–6.93 (d, 1H, J=2.4 Hz, ArH), 6.84–6.87 (d, 1H, J=8.9 Hz, ArH), 6.70–6.72 (dd, 1H, J=9.0 Hz and 2.5 Hz, ArH), 3.86 (s, 2H, CH$_2$), 3.81 (s, 3H, CH$_3$), 2.47 (s, 3H, CH$_3$).

Indomethacin-N-2-(4-methylthiazolyl) amide (compound 57) was obtained upon chromatography on silica gel (EtOAc:hexanes; 30:70 and then 70:30) to afford the pure product as a pale yellow solid which was recrystallized from ethyl ether (241 mg, 63%). $^1$H NMR (CDCl$_3$) δ 8.68 (bs, 1H, NH), 7.70–7.74 (d, 2H, J=9.0 Hz, ArH), 7.48–7.52 (d, 2H, J=9.0 Hz, ArH), 6.79–6.85 (m, 2H, ArH), 6.67–6.71 (dd, 1H, J=9.0 Hz and 2.4 Hz, ArH), 6.52 (s, 1H, Thiazole-H), 3.88 (s, 2H, CH$_2$), 3.79 (s, 3H, CH$_3$), 2.45 (s, 3H, CH$_3$), 2.27 (s, 3H, CH$_3$).

Indomethacin-N-(4-biphenyl) amide (compound 58) was obtained upon chromatography on silica gel (EtOAc:hexanes; 30:70) to afford the pure product as a pale yellow solid (421 mg, 59%). $^1$H NMR (CDCl$_3$) δ 7.68–7.71 (d, 2H, J=8.4 Hz, ArH), 7.32–7.55 (m, 11H, ArH), 6.95–6.96 (d, 1H, J=2.0 Hz, ArH), 6.86–6.89 (d, 1H, J=9.0 Hz, ArH), 6.73–6.74 (dd, 1H, J=1.7 Hz, ArH), 3.83 (s, 2H, CH$_2$), 3.81 (s, 3H, CH$_3$), 2.47 (s, 3H, CH$_3$).

The structures and IC$_{50}$ values for indomethacin and Compounds 28 through 58 are set out in Table 2 below.

TABLE 2

Selective COX-2 Inhibition by Amide Derivatives of Indomethacin

| Compound | R | IC$_{50}$ (μM)[a] COX-2 | COX-1 | Selectivity[b] |
|---|---|---|---|---|
| 1: Indomethacin | OH | 0.75 | 0.05 | 0.066 |
| 28 | NHCH$_3$ | 0.70 | >66[c] | >94 |
| 29 | HN–CH$_2$CH$_2$–OH | 0.25 | >66 | 287 |
| 30 | HN–(CH$_2$)$_7$CH$_3$ | 0.0375 | 66 | 1760 |
| 31 | HN–(CH$_2$)$_9$CH$_3$ | 0.04 | 16.5 | 412.5 |
| 32 | HN–CH$_2$–(2-methylphenyl) | 0.15 | >66[c] | >440 |
| 33 | HN–CH$_2$–(4-methylphenyl) | 0.06 | 8.0 | 133 |
| 34 | HN–CH(CH$_3$)–(4-methylphenyl) (R) | 0.0625 | 4.0 | 64 |
| 35 | HN–CH(CH$_3$)–(4-methylphenyl) (S) | 0.20 | 4.0 | 20 |
| 36 (Comparison) | N(CH$_3$)–CH$_2$CH$_2$–phenyl | >1.0 | >66 | — |

TABLE 2-continued
Selective COX-2 Inhibition by Amide Derivatives of Indomethacin
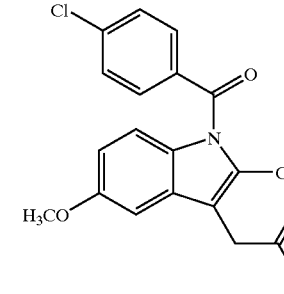
| Compound | R | IC$_{50}$ ($\mu$M)[a] COX-2 | COX-1 | Selectivity[b] |
|---|---|---|---|---|
| 37 (Comparison) | 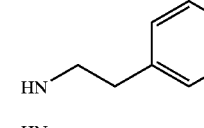 | >1.0 | >66 | — |
| 38 | 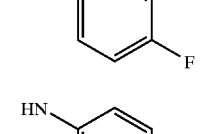 | 0.06 | >66 | >1100 |
| 39 | 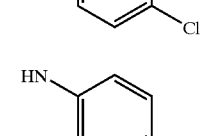 | 0.06 | >66[c] | >1100 |
| 40 | 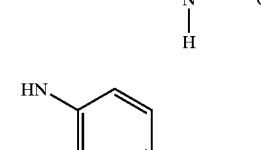 | 0.062 | >66[c] | >1064 |
| 41 | 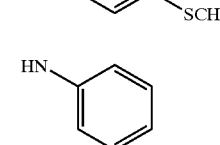 | 0.12 | >66[c] | >550 |
| 42 | 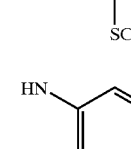 | 0.12 | >66[c] | >550 |
| 43 | 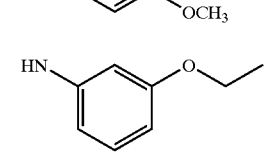 | 0.22 | >66[c] | >300 |
| 44 |  | 0.056 | >66[c] | >1178 |
| 45 | | 0.65 | 52.5 | 81 |

TABLE 2-continued

Selective COX-2 Inhibition by Amide Derivatives of Indomethacin

| Compound | R | IC$_{50}$ ($\mu$M)[a] | | Selectivity[b] |
| --- | --- | --- | --- | --- |
| | | COX-2 | COX-1 | |
| 46 | HN—(3,4,5-trimethoxyphenyl) | >1.0 | >66 | >66 |
| 47 | HN—(pyridin-3-yl) | 0.052 | >66 | >1269 |
| 48 | HN—(6-chloropyridin-3-yl) | 0.047 | >66[c] | >1404 |
| 49 | HN—(1-ethyl-1H-pyrazol-5-yl) | 0.70 | >66[c] | >94 |
| 50 | HN—CH$_2$CH$_2$CH$_2$Cl | 0.050 | 45 | 900 |
| 51 | HN—CH$_2$C(O)OCH$_3$ | 4.0 | >66 | >16.5 |
| 52 | HN—CH(CH$_3$)C(O)OCH$_3$ | 0.4 | >66 | >165 |
| 53 | HN—CH(CH$_3$)C(O)OCH$_3$ | 0.19 | >66 | >347 |
| 54 | HN—CH$_2$—(4-methoxycarbonylphenyl) | 0.080 | >66 | >825 |

TABLE 2-continued

Selective COX-2 Inhibition by Amide Derivatives of Indomethacin

[Structure: indomethacin amide scaffold with 5-methoxy, 2-methyl, N-(4-chlorobenzoyl)indole bearing -CH2-C(=O)-R at the 3-position]

| Compound | R | IC$_{50}$ (μM)[a] COX-2 | COX-1 | Selectivity[b] |
|---|---|---|---|---|
| 55 | 4-(methoxycarbonylmethyl)anilino (HN-C6H4-CH2-C(=O)-OCH3) | 0.058 | >66 | >1138 |
| 56 | 2-pyrazinylamino (HN-pyrazine) | 4.0 | >66 | >16.5 |
| 57 | (4-methylthiazol-2-yl)amino | 4.0 | >66 | >16.5 |
| 58 | 4-biphenylylamino | 0.5 | >66 | >132 |

[a]IC$_{50}$ values were determined by incubating several concn of inhibitor in DMSO with human COX-2 (66 nM) or ovine COX-1 (44 nM) for 20 min followed by treatment with 1-$^{14}$C-AA (50 μM) at 37° C. for 30 sec. Assays were run in duplicate.
[b]Ratio of IC$_{50}$ (COX-1):IC$_{50}$ (COX-2).
[c]>80% remaining COX-1 activity at this concn.

Discussion of Secondary Amide Derivatives of Indomethacin

Carboxylic Acid Aliphatic Secondary Amides Derivatives of Indomethacin.

The N-methyl amide derivative (compound 28) displayed selective COX-2 inhibition (IC$_{50}$ (COX-2)~0.70 μM; IC$_{50}$ (COX-1)>66 μM). Increments in COX-2 inhibitory potency and selectivity was observed with the higher octyl homolog (compound 3); however, further increase in chain length to the nonyl derivative (compound 4) led to some loss of COX-2 selectivity (compound 3: IC$_{50}$ (COX-2)~37.5 nM; IC$_{50}$ (COX-1) 66 μM; compound 4: IC$_{50}$ (COX-2)~40 nM; IC$_{50}$ (COX-1) 16.5 μM).

Carboxylic Acid Aromatic Secondary Amides Derivatives of Indomethacin.

Incorporation of methylene spacer units (compound 38) between the amide nitrogen and the phenyl ring also generated potent and selective COX-2 inhibitors. As observed with the aromatic esters discussed above, selectivity depended on type and position of substituents on the phenyl ring.

For instance, the 4-methylbenzyl amide derivative (compound 33) was 133-fold selective for COX-2, whereas the corresponding 2-methylbenzyl isomer (compound 5) was >440 times more selective as a COX-2 inhibitor. Furthermore, the R-methyl-(4-methylbenzyl) enantiomer (compound 34) was a better inhibitor of COX-2 than the corresponding S-methyl enantiomer (compound 8).

Additionally, the aromatic amides containing the 4-fluoro (compound 39), 4-methylmercapto (compound 15), or the 3-pyridyl substituent (compound 47), displayed potent and selective COX-2 inhibition, as noted below.

Tertiary Amides (Comparison Compounds 36 and 37).

Another interesting aspect in the SAR studies with the indomethacin amides was that N,N-methyl-2-phenethyl (compound 36) and the piperidinyl (compound 37) amide derivatives, both of which are tertiary amides, were inactive against COX-2. In other words, only the secondary amides were selective COX-2 inhibitors, whereas the tertiary amides were devoid of any inhibitory effect towards either isozyme i.e., measurement of COX-2 inhibition for the tertiary amides was stopped at an extremely high IC value (see the value of 33 for both compounds 9 and 10) and still >80% COX-1 activity remained.

Example III

Comparison with Sulfonamides of Another Study.

A similar SAR study was previously reported in the above-noted journal article by Li et al. for acidic sulfonamides. (See, the structures drawn above for compounds L-745,337 and NS-398.) Specifically, Li et al. found that replacement of the N-H proton in the $NHSO_2CH_3$ moiety of L-745,337 or NS-398 with a methyl group lead to complete loss of inhibitory potency towards either the COX-1 or COX-2 isozyme.

This behaviour may be explained from the recently solved crystal structure of murine COX-2 complexed with NS-398. See, Kurumbail et al., Abstract 197, Eicosanoids and Other Bioactive Lipids in Cancer, Inflammation and Related Diseases, Fifth International Conference, La Jolla, Calif. (17–20 Sep. 1997). Unlike the diarylheterocyclics, NS-398 does not utilize the side pocket even though it contains a sulfonamide group. Instead the sulfonamide binds to Arg106 in a fashion similar to the carboxylic acid-containing NSAIDs.

Although the carboxylic acid secondary amide derivatives of indomethacin in the present invention do not contain any electron-withdrawing substituents, the above-discussed SAR observations on the lack of inhibition by the carboxylic acid tertiary amide derivatives suggest that the —CONH— $R_1$ group probably also binds to Arg106. This can be seen from contrasting the data immediately below for the inventive secondary amide derivative (compound 11) with the comparison tertiary amide derivatives (compounds 9 and 10) and the comparison derivative of prior art compound NS-398 in which the N-H proton in the $NHSO_2CH_3$ moiety was replaced with methyl.

Compound 39
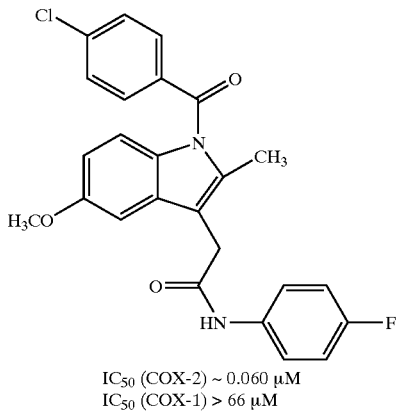
$IC_{50}$ (COX-2) ~ 0.060 µM
$IC_{50}$ (COX-1) > 66 µM

Compound 42
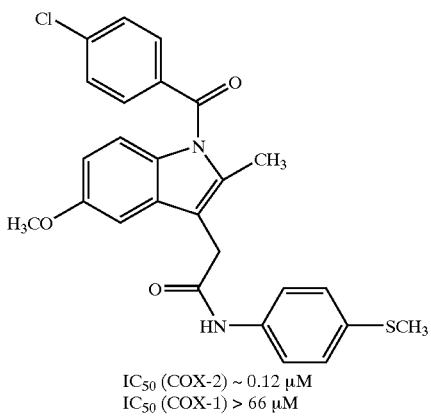
$IC_{50}$ (COX-2) ~ 0.12 µM
$IC_{50}$ (COX-1) > 66 µM

Compound 47
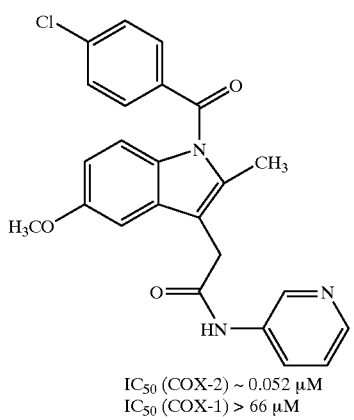
$IC_{50}$ (COX-2) ~ 0.052 µM
$IC_{50}$ (COX-1) > 66 µM

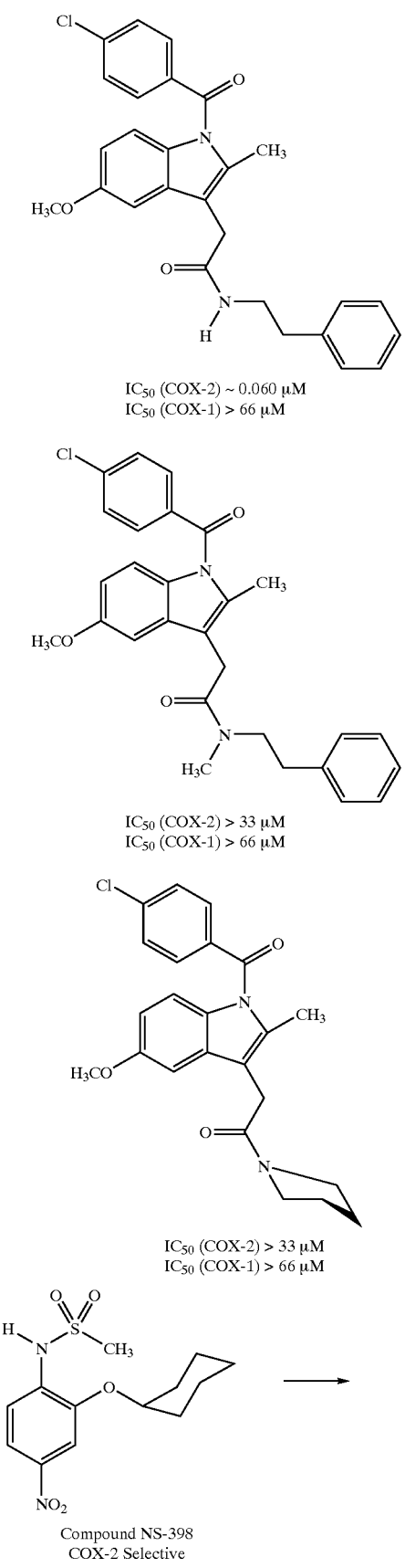

Example IV
Additional Inhibitory Activity Testing with Mouse COX.

Compound 38. The structural basis for COX-2 selectivity by compound 38 also was probed by site directed mutagenesis. More parficularly, the inhibitory potency of indomethacin as compared to that of indomethacin-N-phenethyl amide (compound 38) was evaluated against site directed murine COX-2 mutants (Arg106Gln and Tyr341Ala) which represent key residues involved in the binding of the carboxylic acid-containing NSAIDs. Arg106 is the only positively charged residue in the fatty acid binding site and is important for binding the carboxylic acid moiety of an NSAID with Tyr341Ala, which is juxtaposed to Arg106 at the constriction site and is responsible for the selective binding of the S-enantiomers but not the R-enantiomers in the 2-phenylpropionate class of NSAIDs including flurbiprofen. In addition to these mutants, also analyzed was the inhibition profile of the Val509IleArg499HisVal420Ile mutant (also known as the VRV mutant) which incorporates the major amino acid changes between COX-2 and COX-1 in the side pocket region and is responsible for binding the diarylheterocycles. The results were that indomethacin displayed a slightly better potency against wild-type mouse COX-2 than compound 38 (indomethacin: $IC_{50}$ (mouse COX-2)~25 nM; compound 38: $IC_{50}$ (mouse COX-2)~35 nM). Furthermore, the Tyr341Ala and the triple mutant VRV was resistant to inhibition by each of indomethacin and compound 38, whereas the Arg106Gln mutant was resistant to inhibition by indomethacin but was effectively inhibited by compound 38 ($IC_{50}$~25 nM).

Compound 44. Inhibition of COX-2 activity in intact mouse cells by Compound 44 was assayed in murine RAW264.7 macrophages in which COX-2 activity was induced by pathologic stimuli. The macrophages were treated with LPS (500 ng/mL) and interferon-g (10 U/mL) for 7.5 hours to induce COX-2 and then treated with several concentrations of the 4-methoxyphenyl amide derivative of indomethacin (compound 44) for 30 minutes at 37° C. The $IC_{50}$ value for $PGD_2$ by compound 44 was 62.5 nM. Under these conditions, indomethacin was a better inhibitor of COX-2 activity in intact mouse cells ($IC_{50}$~10 nM) than compound 44.

Indeed, comparison of the potency of indomethacin as a inhibitor of purified mouse COX-2 versus purified human COX-2 revealed that indomethacin displayed greater inhibition of the mouse enzyme than of the human isoform ($IC_{50}$ (mouse COX-2)~350 nM; $IC_{50}$ (human COX-2)~1 μM). On the other hand, an indomethacin-amide derivative (compound 38) was a better inhibitor of human COX-2 than of murine COX-2 (compound 38: $IC_{50}$ (mouse COX-2)~120 nM; $IC_{50}$ (human COX-2)~75 nM).

These results also strengthen another researcher's previous observations which suggest that COX enzymes from the rat are pharmacologically different from those from humans, as reported in Ramesha, "Human and Rat Cyclooxygenases are Pharmacologically Distinct", *Adv. Exp. Med. Biol.* (1997) Vol. 407, pp. 67–71.

Example V

Testing for Reduction in Inflammation.

Compound 41 was tested in a standard in vivo assay of inflammation—the rat foot pad edema model. This assay is widely used in the pharmaceutical industry to evaluate antiinflammatory compounds. Rats were injected with carrageenan, which triggers a rapid edema (swelling) within 3 hours that can be quantitatively measured by volume displacement. A single dose of compound 41 (2 mg/kg) given orally 1 hour after carrageenan injection caused a dramatic decrease in swelling.

In these experiments, the carrageenan that was injected was in 0.1 mL of aqueous saline so that 0.1 mL volume increase was due to the injection alone. Taking this into consideration, approximately an 80–85% reduction in inflammation following treatment with compound 41 was found. For comparison, indomethacin was also tested in this assay at a dose of 2 mg/kg orally, and comparable reduction in inflammation was found.

More specifically, male Sprague-Dawley rats (150 g) received a subplantar injection of carrageenan (0.1 mL of a 1% suspension of carrageenan in sterile aqueous saline) into the right hind footpad while mildly anesthetized with methoxyflurane. At 1 hour post-injection, the rats were gavaged with 0.5 mL corn oil containing either 90 µL DMSO or 90 µL compound 41 for the doses specified below. The ipsilateral footpad volume (mL) was measured with a water displacement plethysmometer at time=3 hours post-injection and compared to the time=0 pre-injection paw volume for edema calculations.

For each dose, 6 rats were injected, and the results are summarized below.

| | Compound 41 | |
| --- | --- | --- |
| Concentration (mg/mL) | 3 hour edema (mL) | standard deviation |
| 0 | 0.87 | 0.1 |
| 0.2 | 0.55 | 0.04 |
| 0.5 | 0.47 | 0.07 |
| 1.0 | 0.39 | 0.03 |
| 2.0 | 0.38 | 0.07 |

It will be understood that various details of the invention may be changed without departing from the scope of the invention. Furthermore, the foregoing description is for the purpose of illustration only, and not for the purpose of limitation--the invention being defined by the claims.

What is claimed is:

1. A method of altering specificity of a cyclooxygenase-inhibiting compound, the method comprising the steps of:
   (a) providing a compound having cyclooxygenase inhibitory activity, the compound having a carboxylic acid moiety or pharmaceutically acceptable salt thereof associated with the cyclooxygenase inhibitory activity and the compound being absent specificity for cyclooxygenase-2 inhibitory activity; and
   (b) altering the specificity of the compound in step (a) from being absent specificity for cyclooxygenase-2 inhibitory activity to having specificity for cyclooxygenase-2 inhibitory activity by converting the compound having the carboxylic acid moiety or pharmaceutically acceptable salt thereof into a derivative having an ester moiety or a secondary amide moiety.

2. The method of claim 1, wherein the compound is a non-steroidal antiinflammatory drug.

3. The method of claim 2, wherein the non-steroidal antiinflammatory drug is selected from the group consisting of fenamic acids, indoles, phenylalkanoic acids, phenylacetic acids, pharmaceutically acceptable salts thereof, and combinations thereof.

4. The method of claim 2, wherein the non-steroidal antiinflammatory drug Is selected from the group consisting of indomethacin, 6-methoxy-α-methyl-2-naphthylacetic acid, meclofenamic acid, diclofenac, flufenamic acid, niflumic acid, mefenamic acid, sulindac, tolmetin, suprofen, ketorolac, flurbiprofen, ibuprofen, aceloferac, alcofenac, amfenac, benoxaprofen, bromfenac, carprofen, clidanac, diflunisal, efenamic acid, etodolic acid, fenbufen, fenclofenac, fenclorac, fenoprofen, fleclozic acid, indoprofen, isofezolac, ketoprofen, loxoprofen, meclofenamate, naproxen, orpanoxin, pirprofen, pranoprofen, tolfenamic acid, zaltoprofen, zomopirac, and pharmaceutically acceptable salts thereof, and combinations thereof.

5. The method of claim 1, wherein the secondary amide derivative is selected from the group consisting of indomethacin-N-methyl amide, indomethacin-N-ethan-2-ol amide, indomethacin-N-octyl amide, indomethacin-N-nonyl amide, indomethacin-N-(2-methylbenzyl) amide, indomethacin-N-(4-methylbenzyl) amide, indomethacin-N-((R)-,4-dimethylbenzyl) amide, indomethacin-N-((S)-,4dimethylbenzyl) amide, indomethacin-N-(2-phenethyl) amide, indomethacin-N-(4-fluorophenyl) amide, indomethacin-N-(4-chlorophenyl) amide, indomethacin-N-(4-acetamidophenyl) amide, indomethacin-N-(4-methylmercapto)phenyl amide, indomethacin-N-(3-methylmercaptophenyl) amide, indomethacin-N-(4-methoxyphenyl) amide, indomethacin-N-(3-ethoxyphenyl) amide, indomethacin-N-(3,4,5-trimethoxyphenyl) amide, indomethacin-N-(3-pyridy) amide, indomethacin-N-5((2-chloro)pyridyl) amide, indomethacin-N-5-((1-ethyl) pyrazolo) amide, indomethacin-N-(3-chloropropyl) amide, indomethacin-N-methoxycarbonylmethyl amide, indomethacin-N-2-(2-L-methoxycarbonylethyl) amide, indomethacin-N-2-(2-D-methoxycarbonylethyl) amide, indomethacin-N-(4-methoxycarbonylbenzyl) amide, indomethacin-N-(4-methoxycarbonylmethylphenyl) amide, indomethacin-N-(2-pyrazinyl) amide, indomethacin-N-2-(4-methylthiazolyl) amide, indomethacin-N-(4-biphenyl) amide, and combinations thereof.

6. A method for analgesic, antiinflammatory, or antipyretic treatment in a warm blooded vertebrate animal, comprising administering to the animal a treatment effective amount sufficient to create an analgesic, antiinflammatory, or antipyretic effect of a carboxylic acid ester derivative or a carboxylic acid secondary amide derivative of a compound, wherein:
   (1) the derivative is selective for inhibition of cyclooxygenase-2, and
   (2) the compound (a) is a cyclooxygenase inhibitor but is absent selectivity for inhibition of cyclooxygenase-2 and (b) contains a carboxylic acid moiety or a pharmaceutically acceptable salt thereof.

7. The method of claim 6, wherein the treatment effective amount sufficient to create an analgesic, antiinflammatory, or antipyretic effect ranges from about 0.5 milligram to about 7.0 milligrams per kilogram of body weight of the animal per day.

8. The method of claim 6, wherein the treatment effective amount sufficient to create an analgesic, antiinflammatory, or antipyretic effect ranges from about 1.5 milligrams to about 6.0 milligrams per kilogram of body weight of the animal per day.

9. The method of claim 6, wherein the treatment effective amount sufficient to create an analgesic, antiinflammatory, or antipyretic effect ranges from about 2.0 milligrams to about 5.0 milligrams per kilogram of body weight of the animal per day.

10. The method of claim 6, wherein the compound is a non-steroidal antiinflammatory drug.

11. The method of claim 10, wherein the non-steroidal antiinflammatory drug is selected from the group consisting of fenamic acids, indoles, phenylalkanoic acids, phenylacetic acids, pharmaceutically acceptable salts thereof, and combinations thereof.

12. The method of claim 10, wherein the non-steroidal antiinflammatory drug is selected from the group consisting of indomethacin, 6-methoxy-α-methyl-2-naphthylacetic acid, meclofenamic acid, diclofenac, flufenamic acid, niflumic acid, mefenamic acid, sulindac, tolmetin, suprofen, ketorolac, flurbiprofen, ibuprofen, aceloferac, alcofenac, amfenac, benoxaprofen, bromfenac, carprofen, clidanac, diflunisal, efenamic acid, etodolic acid, fenbufen, fenclofenac, fenclorac, fenoprofen, fleclozic acid, indoprofen, isofezolac, ketoprofen, loxoprofen, meclofenamate, naproxen, orpanoxin, pirprofen, pranoprofen, tolfenamic acid, zaltoprofen, zomopirac, and pharmaceutically acceptable salts thereof, and combinations thereof.

13. The method of claim 6, wherein the derivative is a derivative of a non-steroidal antiinflammatory drug.

14. The method of claim 13, wherein the derivative is a derivative of a non-steroidal antiinflammatory drug selected from the group consisting of fenamic acids, indoles, phenylalkanoic acids, phenylacetic acids, and combinations thereof.

15. The method of claim 13, wherein the derivative is a derivative of a non-steroidal antiinflammatory drug selected from the group consisting of indomethacin, 6-methoxy-α-methyl-2-naphthylacetic acid, meclofenamic acid, diclofenac, flufenamic acid, niflumic acid, mefenamic acid, sulindac, tolmetin, suprofen, ketorolac, flurbiprofen, ibuprofen, aceloferac, alcofenac, amfenac, benoxaprofen, bromfenac, carprofen, clidanac, diflunisal, efenamic acid, etodolic acid, fenbufen, fenclofenac, fenclorac, fenoprofen, fleclozic acid, indoprofen, isofezolac, ketoprofen, loxoprofen, meclofenamate, naproxen, orpanoxin, pirprofen, pranoprofen, tolfenamic acid, zaltoprofen, zomopirac, and combinations thereof.

16. The method of claim 13, wherein the secondary amide derivative is selected from the group consisting of indomethacin-N-methyl amide, indomethacin-N-ethan-2-ol amide, indomethacin-N-octyl amide, indomethacin-N-nonyl amide, indomethacin-N-(2-methylbenzyl) amide, indomethacin-N-(4-methylbenzyl) amide, indomethacin-N-((R)-,4-dimethylbenzyl) amide, indomethacin-N-((S)-,4-dimethylbenzyl ) amide, indomethacin-N-(2-phenethyl) amide, indomethacin-N-(4-fluorophenyl) amide, indomethacin-N-(4-chlorophenyl) amide, indomethacin-N-(4-acetamidophenyl) amide, indomethacin-N-(4-methylmercapto)phenyl amide, indomethacin-N-(3-methylmercaptophenyl) amide, indomethacin-N-(4-methoxyphenyl) amide, indomethacin-N-(3-ethoxyphenyl) amide, indomethacin-N-(3,4,5-trimethoxyphenyl) amide, indomethacin-N-(3pyridy) amide, indomethacin-N-5-((2-chloro)pyridyl) amide, indomethacin-N-5-((1-ethyl) pyrazolo) amide, indomethacin-N-(3-chloropropyl) amide, indomethacin-N-methoxycarbonylethyl) amide, indomethacin-N-2-(2-L-methoxycarbonylethyl) amide, indomethacin-N-2-(2-D-metoxycarbonylethyl) amide, indomethacin-N-(4-methoxycarbonylbenzyl) amide, indomethacin-N-(4-methoxycarbonylmethylphenyl) amide, indomethacin-N-(2-pyrazinyl) amide, indomethacin-N-2-(4-methylthiazolyl) amide, indomethacin-N-(4-biphenyl) amide, and combinations thereof.

* * * * *